US008980918B2

(12) United States Patent
Betancourt et al.

(10) Patent No.: US 8,980,918 B2
(45) Date of Patent: *Mar. 17, 2015

(54) AMORPHOUS (5-FLUORO-2-METHYL-3-QUINOLIN-2-YLMETHYL-INDOL-1-YL)-ACETIC ACID

(71) Applicant: Atopix Therapeutics Limited, London (GB)

(72) Inventors: Aimesther Betancourt, Laval (CA); Marc Lemieux, Laval (CA); Roch Thibert, Laval (CA)

(73) Assignee: Atopix Therapeutics Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/206,874

(22) Filed: Mar. 12, 2014

(65) Prior Publication Data

US 2014/0255340 A1 Sep. 11, 2014

Related U.S. Application Data

(63) Continuation of application No. 13/414,328, filed on Mar. 7, 2012, now Pat. No. 8,703,956.

(30) Foreign Application Priority Data

Mar. 7, 2011 (GB) .................................. 1103837.9

(51) Int. Cl.
| | | |
|---|---|---|
| A61K 31/04 | (2006.01) | |
| C07D 401/06 | (2006.01) | |
| A61K 31/4709 | (2006.01) | |
| A61K 45/06 | (2006.01) | |
| A61K 9/16 | (2006.01) | |

(52) U.S. Cl.
CPC .......... *C07D 401/06* (2013.01); *A61K 31/4709* (2013.01); *A61K 45/06* (2013.01); *A61K 9/1635* (2013.01); *A61K 9/1652* (2013.01)
USPC .......................................... 514/313; 546/167

(58) Field of Classification Search
USPC .......................................... 546/167; 514/313
See application file for complete search history.

(56) References Cited

U.S. PATENT DOCUMENTS

| | | | |
|---|---|---|---|
| 7,582,672 B2 | 9/2009 | Middlemiss et al. | |
| 7,750,027 B2 | 7/2010 | Armer et al. | |
| 7,919,512 B2 | 4/2011 | Armer et al. | |
| 7,999,119 B2 | 8/2011 | Armer et al. | |
| 8,044,088 B2 | 10/2011 | Armer et al. | |
| 8,163,931 B2 | 4/2012 | Middlemiss et al. | |
| 8,163,936 B2 | 4/2012 | Middlemiss et al. | |
| 8,168,673 B2 | 5/2012 | Armer et al. | |
| 8,198,314 B2 | 6/2012 | Middlemiss et al. | |
| 8,268,878 B2 | 9/2012 | Armer et al. | |
| 8,314,257 B2 | 11/2012 | Middlemiss et al. | |
| 8,536,158 B2 | 9/2013 | Armer et al. | |
| 8,563,536 B2 | 10/2013 | Armer et al. | |
| 8,703,956 B2 * | 4/2014 | Betancourt et al. ........... 546/167 | |
| 2007/0232681 A1 | 10/2007 | Middlemiss et al. | |
| 2009/0186923 A1 | 7/2009 | Armer et al. | |
| 2010/0022613 A1 | 1/2010 | Armer et al. | |
| 2010/0041699 A1 | 2/2010 | Boyd et al. | |
| 2010/0056544 A1 | 3/2010 | Lovell | |
| 2011/0123547 A1 | 5/2011 | Armer et al. | |
| 2011/0124683 A1 | 5/2011 | Hunter et al. | |
| 2011/0142855 A1 | 6/2011 | Armer et al. | |
| 2013/0052190 A1 | 2/2013 | Pearce Collins et al. | |
| 2014/0039012 A1 | 2/2014 | Armer et al. | |

FOREIGN PATENT DOCUMENTS

| | | |
|---|---|---|
| EP | 1 170 594 A2 | 1/2002 |
| EP | 1 211 513 A1 | 6/2002 |
| EP | 0 851 030 B1 | 9/2005 |
| WO | WO 2004/069138 A2 | 8/2004 |
| WO | WO 2005/044260 A1 | 5/2005 |
| WO | WO 2006/092579 A1 | 9/2006 |
| WO | WO 2006/095183 A1 | 9/2006 |
| WO | WO 2007/107772 A1 | 9/2007 |
| WO | WO 2008/012511 A1 | 1/2008 |
| WO | WO 2009/063202 A2 | 5/2009 |
| WO | WO 2009/063215 A2 | 5/2009 |
| WO | WO 2009/090414 A1 | 7/2009 |
| WO | WO 2013/088108 A1 | 6/2013 |
| WO | WO 2013/088109 A1 | 6/2013 |

OTHER PUBLICATIONS

Emery, D.L., et al., "Prostaglandin $D_2$ causes accumulation of eosinophils in the lumen of the dog trachea," *J. Appl. Physiol.* 67: 959-962, American Physiological Society, United States (1989).

Fujitani, Y., et al., "Pronounced Eosinophilic Lung Inflammation and Th2 Cytokine Release in Human Lipocalin-Type Prostaglandin D Synthase Transgenic Mice," *J. Immunol.* 168: 443-449, The American Association of Immunologists, United States (2002).

Gervais, F.G., et al., "Selective modulation of chemokinesis, degranulation, and apoptosis in eosinophils through the $PGD_2$ receptors CRTH2 and DP," *J. Allergy Clin. Immunol.* 108: 982-988, Mosby, Inc., United States (2001).

Hardy, C.C., et al., "The Bronchoconstrictor Effect of Inhaled Prostaglandin $D_2$ in Normal and Asthmatic Men," *N. Engl. J. Med.* 311: 209-213, The Massachusetts Medical Society, United States (1984).

Hirai, H., et al., "Prostaglandin D2 Selectively Induces Chemotaxis in T Helper Type 2 Cells, Eosinophils, and Basophils via Seven-Transmembrane Receptor CRTH2," *J. Exp. Med.* 193: 255-261, The Rockefeller University Press, United States (2001).

Monneret, G., et al., "15R-Methyl-Prostaglandin $D_2$ is a Potent and Selective CRTH2/$DP_2$ Receptor Agonist in Human Eosinophils," *J. Pharmacol. Exp. Ther.* 304: 349-355, The American Society for Pharmacology and Experimental Therapeutics, United States (2003).

Murray, J.J., et al., "Release of Prostaglandin $D_2$ into Human Airways During Acute Antigen Challenge," *N. Engl. J. Med* 315: 800-804, The Massachusetts Medical Society, United States (1986).

Sampson, S.E., et al., "Effect of inhaled prostaglandin $D_2$ in normal and atopic subjects, and of pretreatment with leukotriene $D_4$," *Thorax* 52: 513-518, BMY Publishing Group, England (1997).

International Search Report for International Patent Application No. PCT/EP2012/052504, mailed Apr. 4, 2012, European Patent Office, Rijswijk, Netherlands.

* cited by examiner

*Primary Examiner* — D M Seaman

(74) *Attorney, Agent, or Firm* — Sterne, Kessler, Goldstein & Fox P.L.L.C.

(57) ABSTRACT

The invention relates to a stable amorphous form of (5-Fluoro-2-methyl-3-quinolin-2-ylmethyl-indol-1-yl)-acetic acid and its use in the treatment of conditions mediated by the action of $PGD_2$ at the CRTH2 receptor.

7 Claims, 17 Drawing Sheets

AMORPHOUS (5-FLUORO-2-METHYL-3-QUINOLIN-2-YLMETHYL-INDOL-1-YL)-ACETIC ACID

The present invention relates to a novel stable amorphous form of a compound which is useful as a pharmaceutical, to methods for preparing this amorphous form, compositions containing it and its use in the treatment and prevention of allergic diseases such as asthma, allergic rhinitis and atopic dermatitis and other inflammatory diseases mediated by prostaglandin $D_2$ ($PGD_2$) or other agonists acting at the CRTH2 receptor on cells including eosinophils, basophils and Th2 lymphocytes.

$PGD_2$ is an eicosanoid, a class of chemical mediator synthesised by cells in response to local tissue damage, normal stimuli or hormonal stimuli or via cellular activation pathways. Eicosanoids bind to specific cell surface receptors on a wide variety of tissues throughout the body and mediate various effects in these tissues. $PGD_2$ is known to be produced by mast cells, macrophages and Th2 lymphocytes and has been detected in high concentrations in the airways of asthmatic patients challenged with antigen (Murray et al., (1986), *N. Engl. J. Med.* 315: 800-804). Instillation of $PGD_2$ into airways can provoke many features of the asthmatic response including bronchoconstriction (Hardy et al., (1984) *N. Engl. J. Med.* 311: 209-213; Sampson et al., (1997) *Thorax* 52: 513-518) and eosinophil accumulation (Emery et al., (1989) *J. Appl. Physiol.* 67: 959-962).

The potential of exogenously applied $PGD_2$ to induce inflammatory responses has been confirmed by the use of transgenic mice overexpressing human $PGD_2$ synthase which exhibit exaggerated eosinophilic lung inflammation and Th2 cytokine production in response to antigen (Fujitani et al., (2002) *J. Immunol.* 168: 443-449).

The first receptor specific for $PGD_2$ to be discovered was the DP receptor which is linked to elevation of the intracellular levels of cAMP. However, $PGD_2$ is thought to mediate much of its proinflammatory activity through interaction with a G protein-coupled receptor termed CRTH2 (chemoattractant receptor-homologous molecule expressed on Th2 cells) which is expressed by Th2 lymphocytes, eosinophils and basophils (Hirai et al., (2001) *J. Exp. Med.* 193: 255-261, and EP0851030 and EP-A-1211513 and Bauer et al., EP-A-1170594). It seems clear that the effect of $PGD_2$ on the activation of Th2 lymphocytes and eosinophils is mediated through CRTH2 since the selective CRTH2 agonists 13,14 dihydro-15-keto-$PGD_2$ (DK-$PGD_2$) and 15R-methyl-$PGD_2$ can elicit this response and the effects of $PGD_2$ are blocked by an anti-CRTH2 antibody (Hirai et al., 2001; Monneret et al., (2003) *J. Pharmacol. Exp. Ther.* 304: 349-355). In contrast, the selective DP agonist BW245C does not promote migration of Th2 lymphocytes or eosinophils (Hirai et al., 2001; Gervais et al., (2001) *J. Allergy Clin. Immunol.* 108: 982-988). Based on this evidence, antagonising $PGD_2$ at the CRTH2 receptor is an attractive approach to treat the inflammatory component of Th2-dependent allergic diseases such as asthma, allergic rhinitis and atopic dermatitis.

EP-A-1170594 suggests that the method to which it relates can be used to identify compounds which are of use in the treatment of allergic asthma, atopic dermatitis, allergic rhinitis, autoimmune, reperfusion injury and a number of inflammatory conditions, all of which are mediated by the action of $PGD_2$ or other agonists at the CRTH2 receptor.

Since the publication of EP-A-1170594, there have been a great many publications relating to compounds having CRTH2 antagonist activity. For example, in our earlier applications WO-A-2005/044260, WO2006/095183, WO2008/012511 and WO2009/090414, we describe compounds which are antagonists of $PGD_2$ at the CRTH2 receptor. These compounds are indole-1-acetic acid derivatives substituted at the 3-position with a $CH_2$-aryl group which may be substituted with one or more further substituents. The compounds described in these documents are potent antagonists in vitro of $PGD_2$ at the CRTH2 receptor.

The present invention relates, in particular, to (5-Fluoro-2-methyl-3-quinolin-2-ylmethyl-indol-1-yl)-acetic acid, which is one of the compounds described in WO-A-2005/044260. This compound has proved to be a particularly useful CRTH2 antagonist and has been demonstrated to be effective both in vitro and in vivo. Experiments in which this compound was trialled in man against allergic rhinitis are described in our earlier applications WO 2009/063202 and WO 2009/063215. Furthermore, the compound has been tested and found to be effective both in animal models of asthma and in a clinical trial with human asthma patients (Neil Barnes, Ian Pavord, Alexander Chuchalin, John Bell, Michael Hunter, Mark Payton, Lisa Pearce Collins, Roy Pettipher, Jan Steiner, Michael Perkins; "A randomised, double-blind, placebo-controlled study of the CRTH2 antagonist 00000459 on moderate persistent asthma"; *European Respiratory Journal*, 34, supplement 53, September 2009, 564-565s).

However, 5-Fluoro-2-methyl-3-quinolin-2-ylmethyl-indol-1-yl)-acetic acid (Compound 1) is only sparingly soluble in most pharmaceutically acceptable solvents. The only solvents in which Compound 1 is readily soluble are aqueous alkaline solvents such as sodium hydroxide solution because, under these conditions, Compound 1 is converted into its salt form.

Because of the difficulties in formulating compounds which are not readily soluble in conventional solvents, the present inventors set out to develop a form of the compound which has higher solubility.

One possible solution to the problem of solubility was to develop an amorphous form of Compound 1. However, although amorphous forms are sometimes more soluble than crystalline forms, they are usually associated with their own problems. One such problem is that amorphous forms are very often unstable and revert to a crystalline form after short periods. An unstable amorphous form such as this is therefore not suitable for pharmaceutical use, where it is essential to have a stable physical form of the compound.

Surprisingly, however, the inventors were able to develop an amorphous form of Compound 1 which is stable and does not revert to the crystalline form following prolonged storage.

Therefore, in a first aspect of the invention, there is provided a stable amorphous form of (5-Fluoro-2-methyl-3-quinolin-2-ylmethyl-indol-1-yl)-acetic acid (Compound 1) or a pharmaceutically or veterinarily acceptable salt thereof.

The preparation of this stable amorphous form was by no means straightforward and a number of methods were attempted before it was obtained. Spray drying of Compound 1, which might have been expected to lead to an amorphous form did not do so and the inventors therefore investigated combinations of Compound 1 with various lipidic excipients and polymers. Again, this was not straightforward and conventional methods such as the preparation of hot melt dispersions in lipidic excipients or in polymers did not result in the production of an amorphous product.

A stable amorphous form of Compound 1 was eventually achieved by forming a mixture of the compound with a polymer selected from polyvinylpyrrolidone (PVP), a polyvinylpyrrolidone-vinylacetate copolymer (PVP-VA), hydroxypropylmethylcellulose (HPMC) and hypromellose-acetate-succinate (HPMCAS). It is known to prepare amorphous forms of a compound as a mixture with a polymer but in this case, it proved extremely difficult to find a polymer which provided an amorphous form of Compound 1 which had the necessary stability. Indeed, these were the only polymers tested with which a stable amorphous form could be obtained.

Therefore, the invention further provides a stable composition comprising amorphous (5-Fluoro-2-methyl-3-quinolin-2-ylmethyl-indol-1-yl)-acetic acid (Compound 1) or a pharmaceutically or veterinarily acceptable salt thereof and a polymer selected from polyvinylpyrrolidone (PVP), a polyvinylpyrrolidone-vinylacetate copolymer (PVP-VA), hydroxypropylmethylcellulose (HPMC), hypromellose-acetate-succinate (HPMCAS) and mixtures thereof.

This composition, in addition to the surprising stability of the amorphous Compound 1 was also found to have solubility properties which were greatly superior to what might have been expected. The composition of Compound 1 was highly soluble in simulated gastric fluid and this was indeed surprising since the compound is acidic and crystalline forms have been found to be insoluble in aqueous acids, though they have relatively high solubility at alkaline pH.

In the context of the present invention, the term "amorphous (5-Fluoro-2-methyl-3-quinolin-2-ylmethyl-indol-1-yl)-acetic acid" relates to (5-Fluoro-2-methyl-3-quinolin-2-ylmethyl-indol-1-yl)-acetic acid in which less than about 10%, and preferably less than about 5% of the compound is present in a crystalline form. The presence of crystalline material can be detected by X-ray powder diffraction (XRPD).

The term "stable" relates to a compound which after storage for up to 2 weeks, more suitably up to 4 weeks, still more suitably up to 12 weeks, or at least 12 weeks and especially up to 6 months, particularly at least 6 months at 25° C. and 60% relative humidity, 40° C. and 75% relative humidity or at 50° C. and ambient humidity, when protected from moisture is:
at least 95% chemically identical to the starting sample and retains an amorphous form.

Suitably, a stable compound will be at least 96% and more suitably at least 97% chemically identical to the starting sample and which retains an amorphous form after storage for up to 12 weeks, more suitably at least 12 weeks, protected from moisture at 25° C. and 60% relative humidity, 40° C. and 75% relative humidity or at 50° C. and ambient humidity.

In particular, a stable compound may be at least 95%, at least 96%, at least 97% or even at least 98% chemically identical to the starting sample and which retains an amorphous form after storage for up to 6 months, especially at least 6 months, at 25° C. and 60% relative humidity or at 40° C. and 75% relative humidity when protected from moisture.

In some cases, the stable compound may be at least 99% chemically identical to the starting sample and which retains an amorphous form after storage for up to 6 months, especially at least 6 months, at 25° C. and 60% relative humidity when protected from moisture.

Chemical identity to the starting material may be determined using high performance liquid chromatography (HPLC).

Appropriate pharmaceutically and veterinarily acceptable salts of the compounds of general formulae (I) and (II) include basic addition salts such as sodium, potassium, calcium, aluminium, zinc, magnesium and other metal salts as well as choline, diethanolamine, ethanolamine, ethyl diamine, megulmine and other well known basic addition salts as summarised in Paulekuhn et al., (2007) *J. Med. Chem.* 50: 6665-6672 and/or known to those skilled in the art.

The sodium and potassium salts are particularly suitable for use in the present invention, more especially the sodium salt.

In some circumstances, more stable compositions are obtained using Compound 1 as the free acid rather than in the form of a salt.

Suitably, the weight ratio of polymer to Compound 1 or salt thereof is at least 1.5:1, for example from 1.5:1 to 15:1, though more usually, it is from 1.5:1 to 12:1. Most suitably, the weight ratio of polymer to Compound 1 or salt thereof is from about 1.5:1 to 9:1.

Although PVP, PVP-VA, HPMC, HPMCAS and mixtures of these polymers may all be used to form the compositions of the present invention, PVP, HPMC, PVP-VA and mixtures thereof are particularly suitable. Still more suitable compositions may be formed using PVP and PVP-VA, and the most stable amorphous compositions are formed using PVP.

When PVP-VA is used in the composition of the present invention, a particularly suitable form is a copolymer of 1-vinyl-2-pyrrolidone and vinyl acetate in a ratio of 6:4 by mass. A suitable polymer is sold under the trade mark Kollidon VA 64.

Any polyvinylpyrrolidone (PVP) is suitable for use in the composition of the invention, for example PVP K12, PVP K17, PVP K25 or PVP K30. A particularly suitable material is PVP K30, although suitable compositions have also been successfully prepared using other PVP materials such as PVP K12.

The compositions of the invention are typically solid dispersions of Compound 1 or a pharmaceutically or veterinarily acceptable salt thereof in polymer and can be formed by conventional methods such as mixing followed by solvent evaporation or, more usually, by spray drying.

A solid dispersion according to the invention may be prepared by a process comprising:
ia. dissolving the polymer in a first solvent at a concentration of from 50-110 g/L;
iia. adding solid crystalline Compound 1 or a pharmaceutically or veterinarily acceptable salt thereof to the solution to form a suspension, wherein the weight ratio of polymer to Compound 1 or salt thereof is at least 1.5:1, typically from about 1.5:1 to 15:1;
iiia. adding a second solvent, wherein the second solvent is chosen such that it is suitable to solubilise Compound 1 or the salt thereof and wherein the volume ratio of second solvent to first solvent is from 0.1:1 to 0.5:1;
iva. stirring the mixture at about 5 to 60° C. until a solution is obtained;
va. removing solvent until the volume of solvent remaining is from about 20-50% of the total volume of solvent originally added; and either via. evaporating the solution to dryness; or
viia adding a third solvent, wherein the third solvent is chosen such that it is suitable to solubilise Compound 1 or the salt thereof and wherein the amount of the third solvent is such that the total solids concentration in the solution (i.e. concentration of polymer+Compound 1) is from 5 to 15%; and
viiia. spray drying the solution obtained in (viia) to obtain a solid dispersion of Compound 1 or the salt thereof in polymer according to the invention.

In (ia) above, the first solvent is selected from suitable organic solvents, for example methanol, dichloromethane or a mixture thereof. A particularly suitable first solvent for use in (ia) is a 1:1 mixture (by volume) of methanol and dichloromethane. A more suitable concentration for the solution is from 60-100 g/L, typically 70-90 g/L.

In (iia) above, the amount of Compound 1 or the salt thereof is suitably chosen such that the weight ratio of polymer to Compound 1 or the salt thereof is from 1.5:1 to 12:1, most suitably from about 1.5:1 to 9:1.

In (iiia) above, DMSO is a particularly suitable second solvent and the volume ratio of second solvent to first solvent is more usually from 0.2:1 to 0.4:1 and typically about 0.3:1.

In (iva), stirring usually takes place for a period of about 20-90 minutes, more typically about 25-70 minutes and especially about 30-60 minutes. Stirring is generally carried out at about 5-30° C., more usually at room temperature, i.e. about 16-25° C.

In (va), the solvent is usually removed by evaporation, which may be achieved by direct heating in which the temperature is typically increased from room temperature to a temperature of about 100 to 120° C. Alternatively, the solvent can be partially removed by heating the solution in a water bath at 100° C. Heating of the solution may be continued until a suitable amount of solvent has been removed and this is generally when the volume of solvent remaining is from about 20-50% of the total volume of solvent added (i.e. the total volume of the first and second solvents), suitably 25-45% of the total volume of solvent added and especially about 30-40% of the total volume of solvent added. The time taken to achieve this may vary depending upon the starting volume of solvent.

After (va), a solid dispersion may be obtained by simply removing the remainder of the solvent by evaporating the solution to dryness. It is, however, preferable to obtain the solid dispersion by spray drying as set out in (viia) and (viiia). In (viia) suitable third solvents include DMSO, acetone and mixtures thereof, especially DMSO or a mixture of DMSO and acetone is in a ratio of 1:1 to 1:3 DMSO to acetone, more usually about 1:2 DMSO to acetone, e.g about 1.8:1 to 1:1. The total solids concentration of the final solution is more usually 7-12% and typically 8-10% w/v.

In an alternative process, a solid dispersion according to the invention may be prepared by a process comprising:

ib. preparing a solution of Compound 1 and a polymer in a suitable solvent, wherein:
the weight ratio of polymer to Compound 1 or salt thereof is at least 1.5:1, typically from about 1.5:1 to 15:1; and
the ratio of Compound 1:solvent is from about 1:35 to 1:65 w/v; and iib. spray drying the solution obtained in (i) to obtain a solid dispersion of Compound 1 or the salt thereof in polymer according to the invention.

Typically, the solvent used in step (ib) is a mixture of DMSO and acetone, with the ratio of DMSO to acetone being from about 25:75 to 45:55, more usually from about 30:70 and 40:60 and typically about 35:65.

Thus, the ratio of Compound 1:DMSO will vary from about 1:12.5 to 1:22.5 w/v, usually about 1:15 to 1:20 and typically about 1:17.5 w/v; and
the ratio of Compound 1:acetone will vary from about 1:37.5 to 1:27.5 w/v, usually about 1:35 to 1:30 and typically about 1:32.5 w/v.

When the solvent is a mixture of DMSO and acetone, the solution of step (ib) may be prepared by adding the polymer and Compound 1 or a pharmaceutically or veterinarily acceptable salt thereof to the appropriate amount of DMSO and subsequently adding acetone.

In general, the DMSO solution will be heated, usually to a temperature of about 90-110° C., usually about 100° C. before adding the acetone. The acetone may be added under reflux and the solution allowed to cool to about 50-70° C., more usually 55-60° C. This temperature is typically maintained during the spray drying step (iib).

The spray drying of steps (viiia) and (iib) is carried out under standard conditions using nitrogen as the atomisation gas and air as the drying gas. Typically, when conducted on a laboratory scale as illustrated in the examples below, the nitrogen flow rate is about 465-480 L/h, for example about 473 L/h and the air flow is 90-100% (corresponding to about 35-40 m³/hour. A suitable nozzle size is 1-2 mm and the feed rate used may be about 3-15 mL/minute. The inlet temperature may range from about 140 to 230° C. and the outlet temperature from about 75 to 130° C. A person skilled in the art of spray drying would have no difficulty in selecting appropriate conditions for larger batches.

In a further aspect of the invention there is provided stable amorphous Compound 1 or a pharmaceutically or veterinarily acceptable salt thereof or a composition as defined above comprising amorphous Compound 1 or a pharmaceutically or veterinarily acceptable salt thereof for use in medicine, particularly in the treatment or prevention of asthma, asthma exacerbations, chronic obstructive pulmonary disease, allergic rhinitis, conjunctivitis, nasal polyps, atopic dermatitis, contact hypersensitivity (including contact dermatitis), eosiniphilic cough, eosinophilic bronchitis, eosinophilic gastroenteritis, eosinophilic oesophagitis, food allergies, inflammatory bowel disease, ulcerative colitis, Crohn's disease, mastocytosis, urticaria, hypereosinophilic syndrome, hyper IgE syndrome, fibrotic diseases, Churg-Strauss syndrome and multiple sclerosis.

The compound is also of use in the treatment of infection.

The term "asthma" includes all types of asthma, for example allergic asthma, non allergic asthma, eosinophilic asthma, steroid resistant asthma, Th2 dependent asthma, non-Th2 dependent asthma and aspirin induced asthma. In one embodiment, the asthma is allergic asthma and in another embodiment the asthma is eosinophilic asthma.

"Asthma exacerbations" includes exacerbations induced by viral infections, especially infection with respiratory syncytial virus (RSV) or rhinovirus.

Allergic rhinitis includes both perennial allergic rhinitis and seasonal allergic rhinitis.

"Conjunctivitis" includes, in particular, allergic conjunctivitis, vernal keratoconjunctivitis and atopic keratoconjunctivitis.

"Infection" includes bacterial, viral or fungal infection. The infection may occur in patients who are atopic or are at risk of becoming atopic and may be, for example a rhinovirus, influenza or RSV infection, especially in asthmatic patients. Alternatively, the infection may be a bacterial infection for example a *Staphylococcus aureus* infection, particularly in patients suffering from atopic dermatitis.

The term "fibrotic diseases" includes, in particular, fibrotic diseases caused/exacerbated by Th2 immune responses, for example idiopathic pulmonary fibrosis, scleroderma and hypertrophic scars.

The amorphous form of Compound 1 or the composition of the invention may also be of use in the treatment of other PGD2-mediated diseases. Diseases which may be mediated by PGD2 include autoimmune diseases such as systemic lupus erythematus, psoriasis, acne, allograft rejection, rheumatoid arthritis, psoriatic arthritis and osteoarthritis.

The invention further provides a method for the treatment or prevention of a disease or condition selected from those listed above, the method comprising administering to a patient in need of such treatment an effective amount of stable amorphous Compound 1 or a pharmaceutically or veterinarily acceptable salt thereof or a composition as defined above comprising amorphous Compound 1.

There is also provided the use of stable amorphous Compound 1 or a pharmaceutically or veterinarily acceptable salt thereof or a composition as defined above in the preparation of an agent for the treatment or prevention of a disease or condition selected from those listed above.

Stable amorphous Compound 1 or the composition defined above comprising amorphous compound 1 must be formulated in an appropriate manner depending upon the diseases or conditions it is required to treat.

The patient will be a mammal, for example a human.

Therefore, in a further aspect of the invention there is provided a pharmaceutical or veterinary composition comprising a composition comprising amorphous Compound 1 or a pharmaceutically or veterinarily acceptable salt thereof or a composition as defined above together with a pharmaceutically acceptable excipient. Other active materials may also be present, as may be considered appropriate or advisable for the disease or condition being treated or prevented.

The excipient, or, if more than one be present, each of the excipients, must be acceptable in the sense of being compatible with the other ingredients of the formulation and not deleterious to the recipient.

The formulations include those suitable for oral (including viscous oral formulations), rectal, nasal, bronchial (inhaled), topical (including eye drops, buccal, oral viscous and sublingual), vaginal or parenteral (including subcutaneous, intramuscular, intravenous and intradermal) administration and may be prepared by any methods well known in the art of pharmacy.

The route of administration will depend upon the condition to be treated but preferred compositions are formulated for oral, nasal, bronchial or topical administration.

The composition may be prepared by bringing into association the amorphous Compound 1 or salt thereof with the excipient. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing the composition defined above comprising amorphous Compound 1 in conjunction or association with a pharmaceutically or veterinarily acceptable carrier or vehicle.

Formulations for oral administration in the present invention may be presented as: discrete units such as capsules, sachets or tablets each containing a predetermined amount of the amorphous Compound 1 or salt thereof; as a powder or granules; as a solution or a suspension of amorphous Compound 1 in an aqueous liquid or a non-aqueous liquid; or as an oil-in-water liquid emulsion or a water in oil liquid emulsion; or as a bolus etc.

For compositions for oral administration (e.g. tablets, capsules, formulations comprising a mucoadherent etc), the term "acceptable carrier" includes vehicles such as common excipients e.g. binding agents, for example syrup, acacia, gelatin, sorbitol, tragacanth, polyvinylpyrrolidone (povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; wetting agents/surfactants such as poloxamers, polysorbates, sodium docusate and sodium lauryl sulfate; disintegrants such as starch or sodium starch glycolate; and lubricants such as magnesium stearate, sodium stearate and other metallic stearates, glycerol stearate, stearic acid, silicone fluid, talc waxes, oils and colloidal silica. Sweetening agents and flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the amorphous Compound 1 in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Some formulations may comprise a mucoadherent, for example a mucopolysaccharide such as sodium hyaluronate. Such compositions may be formulated as, for example, liquids, liquid syrups, soft gels, liquid gels, flowable gels or aqueous suspensions and may, in addition to the active agent and the mucoadherent, also contain one or more additional excipients as set out above. Liquid formulations will usually also contain a liquid carrier, which may be a solvent or suspending agent, for example water or saline solution and may also contain a substance to increase their viscosity, for example sodium carboxymethylcellulose, sorbitol or dextran.

Other formulations suitable for oral administration include lozenges comprising the active agent in a flavoured base, usually sucrose and acacia or tragacanth; pastilles comprising the amorphous Compound 1 in an inert base such as gelatin and glycerin, or sucrose and acacia; and mouthwashes comprising the active agent in a suitable liquid carrier.

For topical application to the skin, the composition may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

The composition defined above may be used for the treatment of the respiratory tract by nasal, bronchial or buccal administration of, for example, aerosols or sprays which can disperse the pharmacological active ingredient in the form of a powder or in the form of drops of a solution or suspension. Pharmaceutical compositions with powder-dispersing properties (e.g., dry powder inhalers) usually contain, in addition to the active ingredient, a suitable carrier such lactose and, if desired, adjuncts, such as surfactants and/or diluents and/or flow aids and/or lubricants. Pharmaceutical compositions with powder-dispersing properties (e.g., metered dose inhalers) usually contain, in addition to the active ingredient, a liquid propellant with a boiling point below room temperature and, if desired, adjuncts, such as liquid or solid non-ionic or anionic surfactants and/or diluents. Pharmaceutical compositions in which the pharmacological active ingredient is in solution (e.g., either solution for nebulisation or metered dose inhalers) contain, in addition to this, a suitable propellant, and furthermore, if necessary, an additional solvent and/or a stabiliser. Instead of the propellant, compressed air can also be used, it being possible for this to be produced as required by means of a suitable compression and expansion device.

Parenteral formulations will generally be sterile.

Typically, the dose of Compound 1 will be about 1 to 400 mg per day, more usually 10 to 400 mg per day. The dose will be chosen so as to maintain the concentration of drug in the plasma at a level effective to inhibit $PGD_2$ at the CRTH2 receptor. The precise amount of Compound 1 which is therapeutically effective, and the route by which such compound is best administered, is readily determined by one of ordinary skill in the art by comparing the blood level of the agent to the concentration required to have a therapeutic effect.

The pharmaceutical composition is most suitably formulated as a once-a-day administration, although more frequent dosing may be used in some cases, for example twice, three times or four times daily dosing. On the other hand, it may sometimes be possible to dose less frequently than once daily, for example once every two days. In some circumstances a dosage regimen may be used in which the composition is administered for a first period and then, during a second period, administration ceases or, alternatively, the composition administered at a lower dose. Such a dosage regimen is described in WO 2009/063202.

The composition as defined above may be used in combination with one or more active agents which are useful in the treatment of the diseases and conditions listed above, although these active agents are not necessarily inhibitors of $PGD_2$ at the CRTH2 receptor.

Therefore, the pharmaceutical composition described above may additionally contain one or more of these active agents.

There is also provided the use of the composition as defined above in the preparation of an agent for the treatment of diseases and conditions mediated by CRTH2 receptor agonists, especially $PGD_2$, wherein the agent also comprises an additional active agent useful for the treatment of the same diseases and conditions.

These additional active agents may be other CRTH2 receptor antagonists or may have a completely different mode of action. They include existing therapies for allergic and other inflammatory diseases including:

Suplatast tosylate and similar compounds;

$\beta 2$ adrenoreceptor agonists such as metaproterenol, isoproterenol, isoprenaline, albuterol, salbutamol, formoterol, salmeterol, indacaterol, terbutaline, orciprenaline, bitolterol mesylate and pirbuterol or methylxanthines such as theophylline, oxitriphylline and aminophylline, mast cell stabilisers such as sodium cromoglycate or muscarinic receptor antagonists such as tiotropium, aclidinium and ipratropium; antihistamines, for example histamine $H_1$ receptor antagonists such as loratadine, cetirizine, desloratadine, levocetirizine, fexofenadine, astemizole, azelastine, olopatadine and chlorpheniramine or $H_4$ receptor antagonists;

$\alpha_1$ and $\alpha_2$ adrenoreceptor agonists such as propylhexedrine phenylephrine, phenylpropanolamine, pseudoephedrine, naphazoline hydrochloride, oxymetazoline hydrochloride, tetrahydrozoline hydrochloride, xylometazoline hydrochloride and ethylnorepinephrine hydrochloride;

modulators of chemokine receptor function, for example CCR1, CCR2, CCR2A, CCR2B, CCR3, CCR4, CCR5, CCR6, CCR7, CCR8, CCR9, CCR10 and CCR11 (for the C—C family) or CXCR1, CXCR2, CXCR3, CXCR4 and CXCR5 (for the C—X—C family) and $CX_3CR1$ for the C—$X_3$—C family;

Leukotriene antagonists such as montelukast, pranlukast and zafirlukast leukotriene biosynthesis inhibitors such as 5-lipoxygenase inhibitors or 5-lipoxygenase activating protein (FLAP) inhibitors such as zileuton, ABT-761, fenleuton, tepoxalin, Abbott-79175, N-(5-substituted)-thiophene-2-alkylsolfonamides, 2,6-di-tert-butylphenol hydrazones, methoxytetrahydropyrans such as ZD2138, SB-210661, pyridinyl-substituted-2-cyanonaphthalene compounds such as L-739010, 2-cyanoquinoline compounds such as L-746,530, indole and quinoline compounds such as MK-591, MK-886 and BAY x 1005; Phosphodiesterase inhibitors, including PDE4 inhibitors such as roflumilast;

anti-IgE antibody therapies such as omalizumab;

anti-infectives such as fusidic acid (particularly for the treatment of atopic dermatitis);

anti-fungals such as clotrimazole (particularly for the treatment of atopic dermatitis); immunosuppressants such as tacrolimus and particularly pimecrolimus in the case of inflammatory skin disease or alternatively FK-506, rapamycin, cyclosporine, azathioprine or methotrexate;

Immunotherapy agents including allergen immunotherapy such as Grazax; corticosteroids such as prednisone, prednisolone, flunisolide, ciclesonide, triamcinolone acetonide, beclomethasone dipropionate, budesonide, fluticasone propionate mometasone furoate and fluticasone furoate;

drugs which promote Th1 cytokine response such as interferons, TNF or GM-CSF. CRTH2 antagonists may also be combined with therapies that are in development for inflammatory indications including:

other antagonists of $PGD_2$ acting at other receptors such as DP antagonists;

drugs that modulate cytokine production such as inhibitors of TNFα converting enzyme (TACE) anti-TNF monoclonal antibodies, TNF receptor immunoglobulin molecules, inhibitors of other TNF isoforms, non-selective COX-1/COX-2 inhibitors such as piroxicam, diclofenac, propionic acids such as naproxen, flubiprofen, fenoprofen, ketoprofen and ibuprofen, fenamates such as mefanamic acid, indomethacin, sulindac and apazone, pyrazolones such as phenylbutazone, salicylates such as aspirin; COX-2 inhibitors such as meloxicam, celecoxib, rofecoxib, valdecoxib and etoricoxib, low dose methotrexate, lefunomide, ciclesonide, hydroxychloroquine, d-penicillamine, auranofin or parenteral or oral gold; drugs that modulate the activity of Th2 cytokines including IL-4, IL-5, IL-9, IL-13 and their receptors, for example blocking monoclonal antibodies (e.g. mepolizumab) and soluble receptors;

PPAR-γ agonists such as rosiglitazone, piaglitazone; or with anti-RSV antibodies such as Synagis (palivizumab) and agents that may be used to treat rhinovirus infection in the future e.g. interferon-alpha, interferon-beta or other interferons.

Combinations of stable amorphous Compound 1 or of the composition as defined above with leukotriene antagonists such as montelukast, pranlukast and zafirlukast are particularly suitable, especially combinations with montelukast.

Other particularly suitable combinations of stable amorphous Compound 1 or of the composition as defined above are those with histamine $H_1$ receptor antagonists such as loratadine, cetirizine, desloratadine, levocetirizine, fexofenadine, astemizole, azelastine, olopatadine and chlorpheniramine.

In yet a further aspect of the invention, there is provided a product comprising stable amorphous Compound 1 or the composition as defined above and one or more of the agents listed above as a combined preparation for simultaneous, separate or sequential use in the treatment of a disease or condition mediated by the action of $PGD_2$ at the CRTH2 receptor.

In yet another aspect of the invention, there is provided a kit for the treatment of a disease or condition mediated by the action of $PGD_2$ at the CRTH2 receptor comprising a first container comprising the composition as defined above and a second container comprising one or more of the active agents listed above.

The invention will now be described in greater detail with reference to the examples and to the figures in which.

Figure 9:
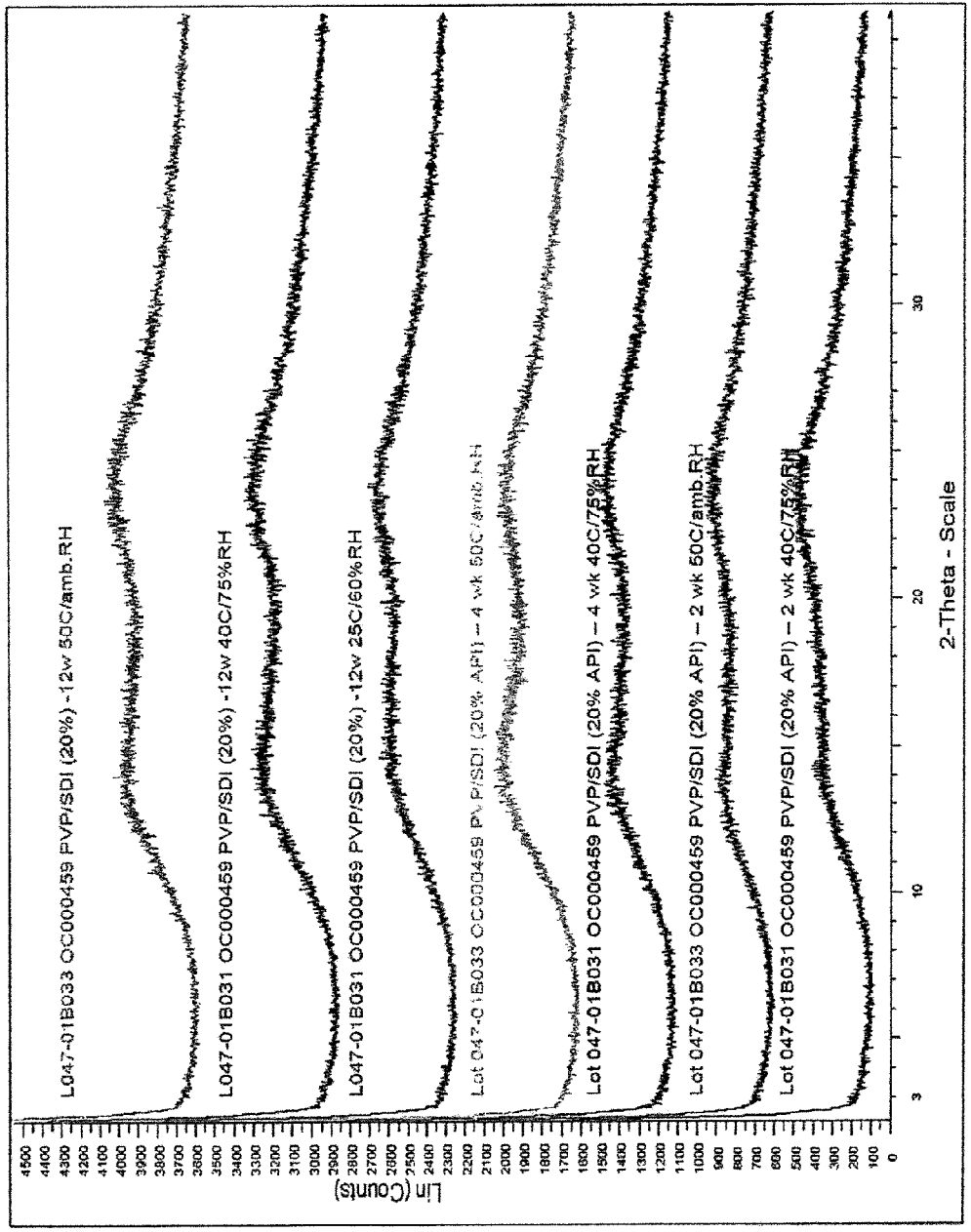

FIG. 9 shows XRPD data for PVP SDI lots 031 and 033 after 2, 4 and 12 weeks.

Figure 10:
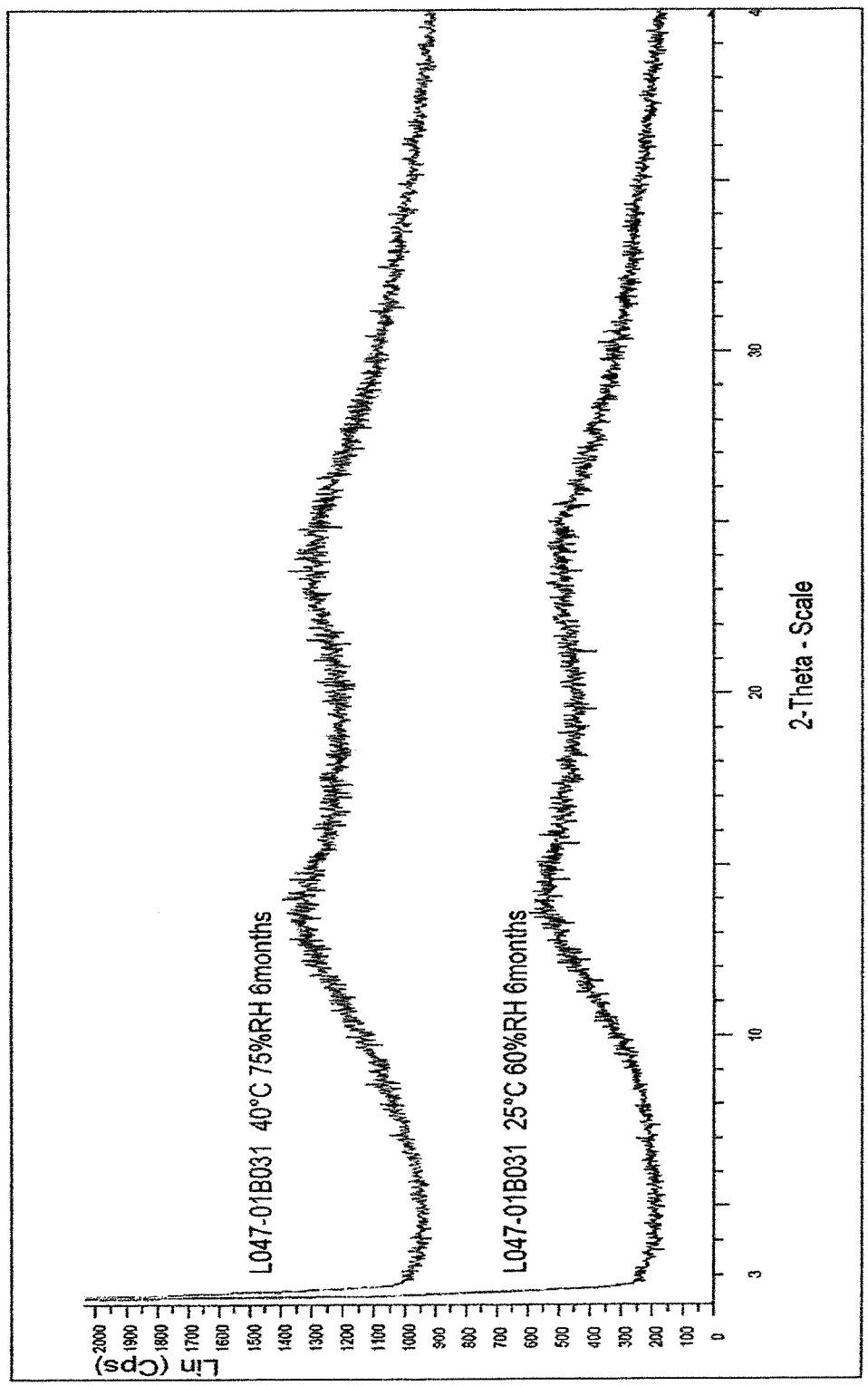

FIG. 10 shows XRPD data for PVP SDI lot 031 after 6 months.

Figure 11:
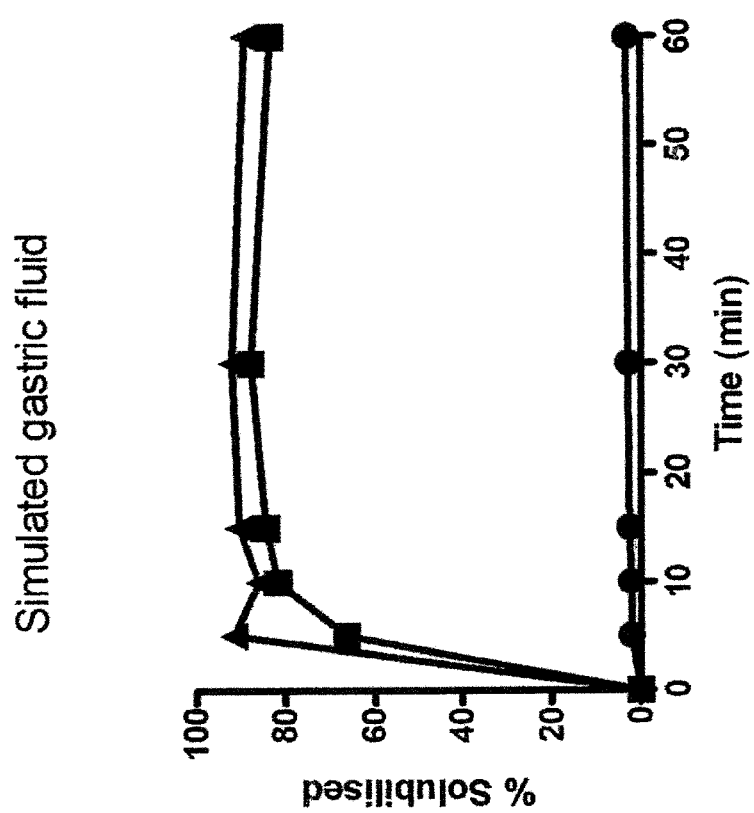

FIG. 11 is a solubility plot of crystalline Compound 1, Lot 031 and Lot 033 in USP simulated gastric fluid at pH 1.2; results expressed on the primary Y axis as a percentage of material in solution with respect to the standard at 0.1209 mg/ml, and on the secondary Y axis as absolute amount of material dissolved in mg/ml. In FIG. 11:

— represents Lot 031
— represents Lot 033
— represents crystalline Compound 1

Figure 12:
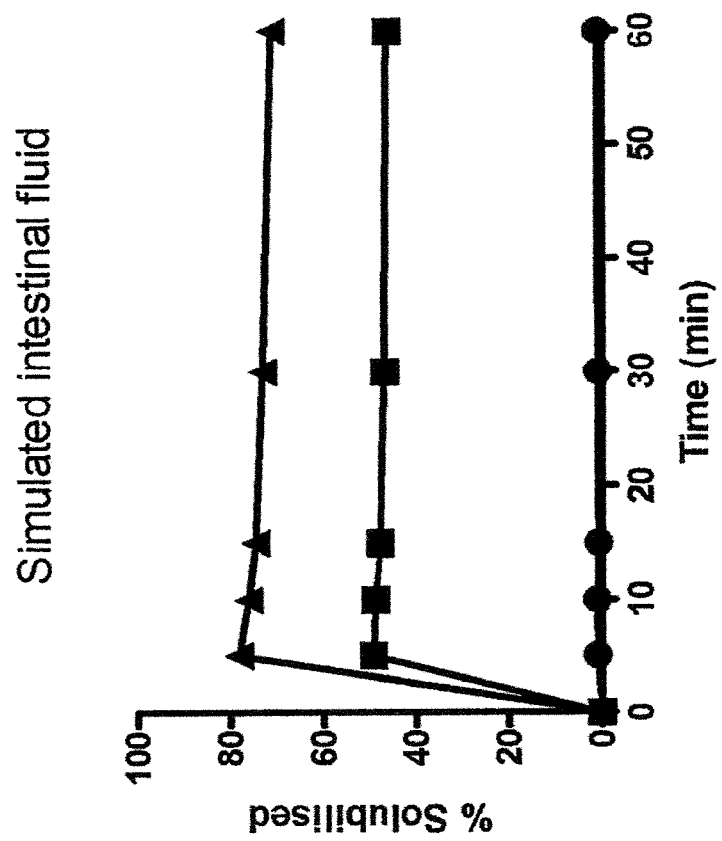

FIG. 12 is a solubility plot of crystalline Compound 1, Lot 031 and Lot 033 in USP simulated intestinal fluid at pH 6.8; results expressed on the primary Y axis as a percentage of material in solution with respect to the standard at 0.1209 mg/ml, and on the secondary Y axis as absolute amount of material dissolved in mg/ml. In FIG. 12:

— represents Lot 031
— represents Lot 033
— represents crystalline Compound 1

Figure 13:
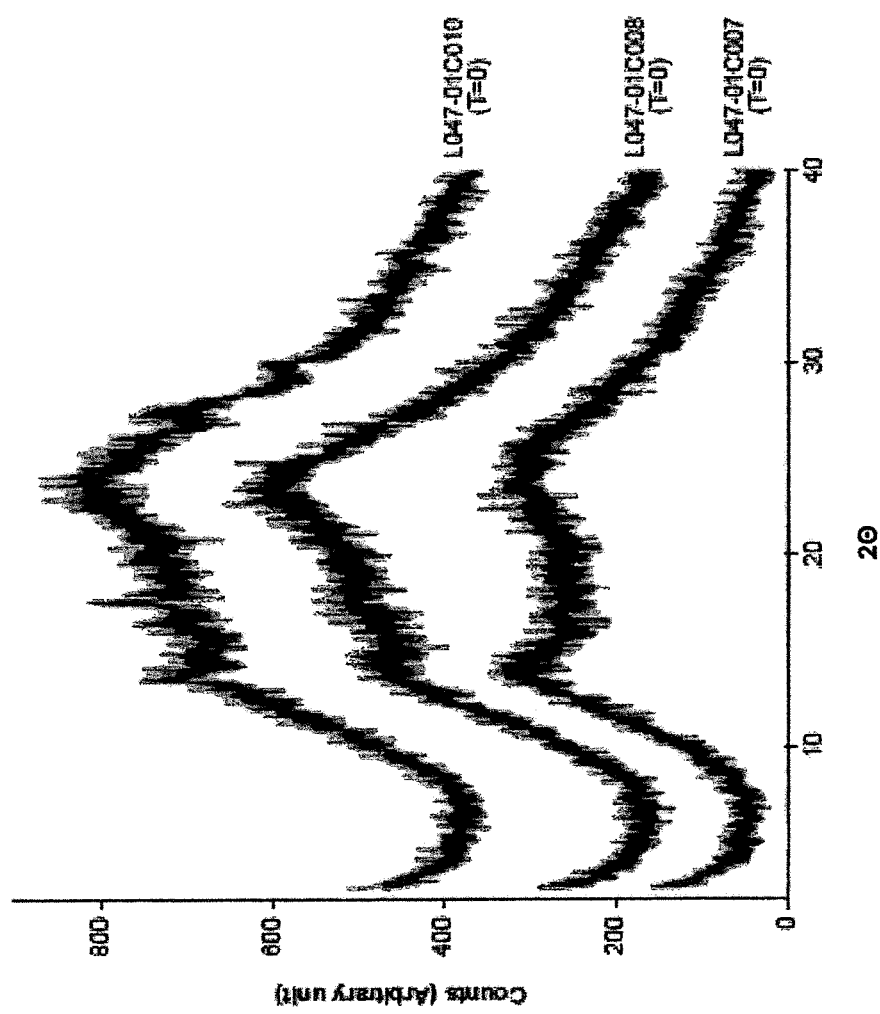

FIG. 13 shows XRPD diffractograms for Lots C007, C008 and C010 at T=0 in the stability trial.

Figure 14:
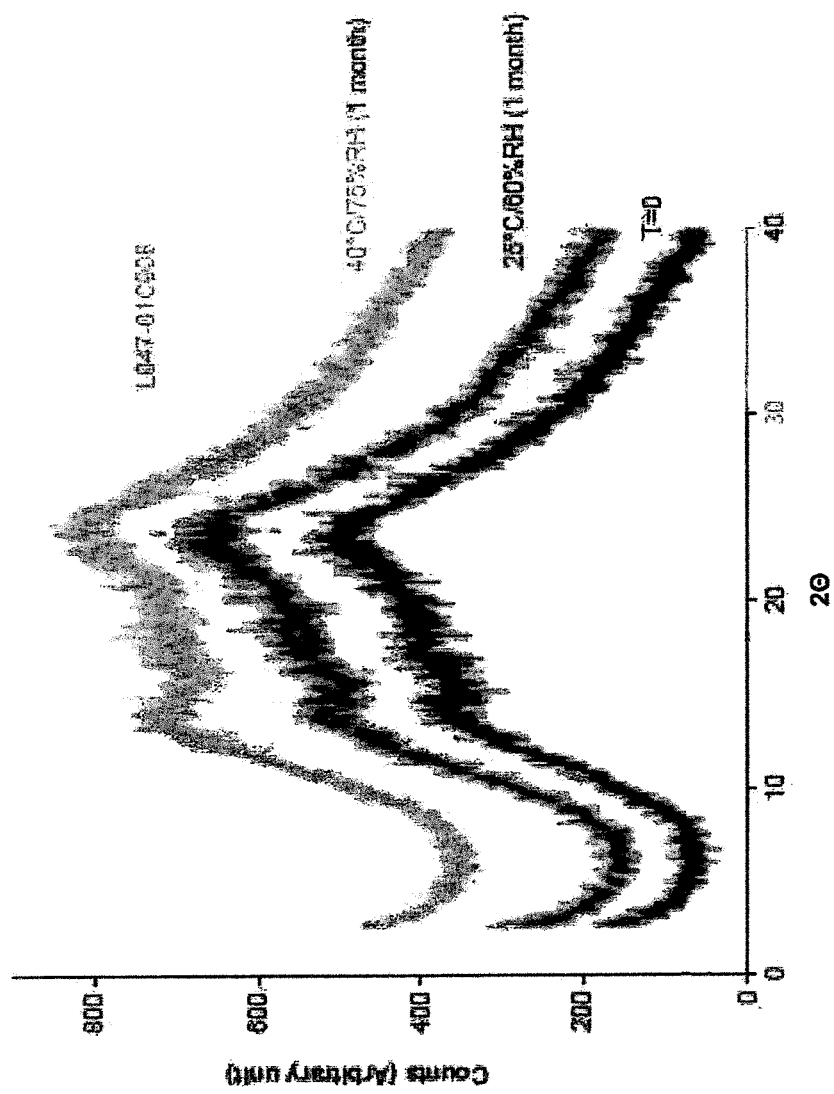

FIG. 14 shows XRPD diffractograms for Lot C008 at T=0 (black trace) after 1 month at 25° C./60% RH (red trace) and after 1 month at 40° C./75% RH (green trace).

Figure 15:
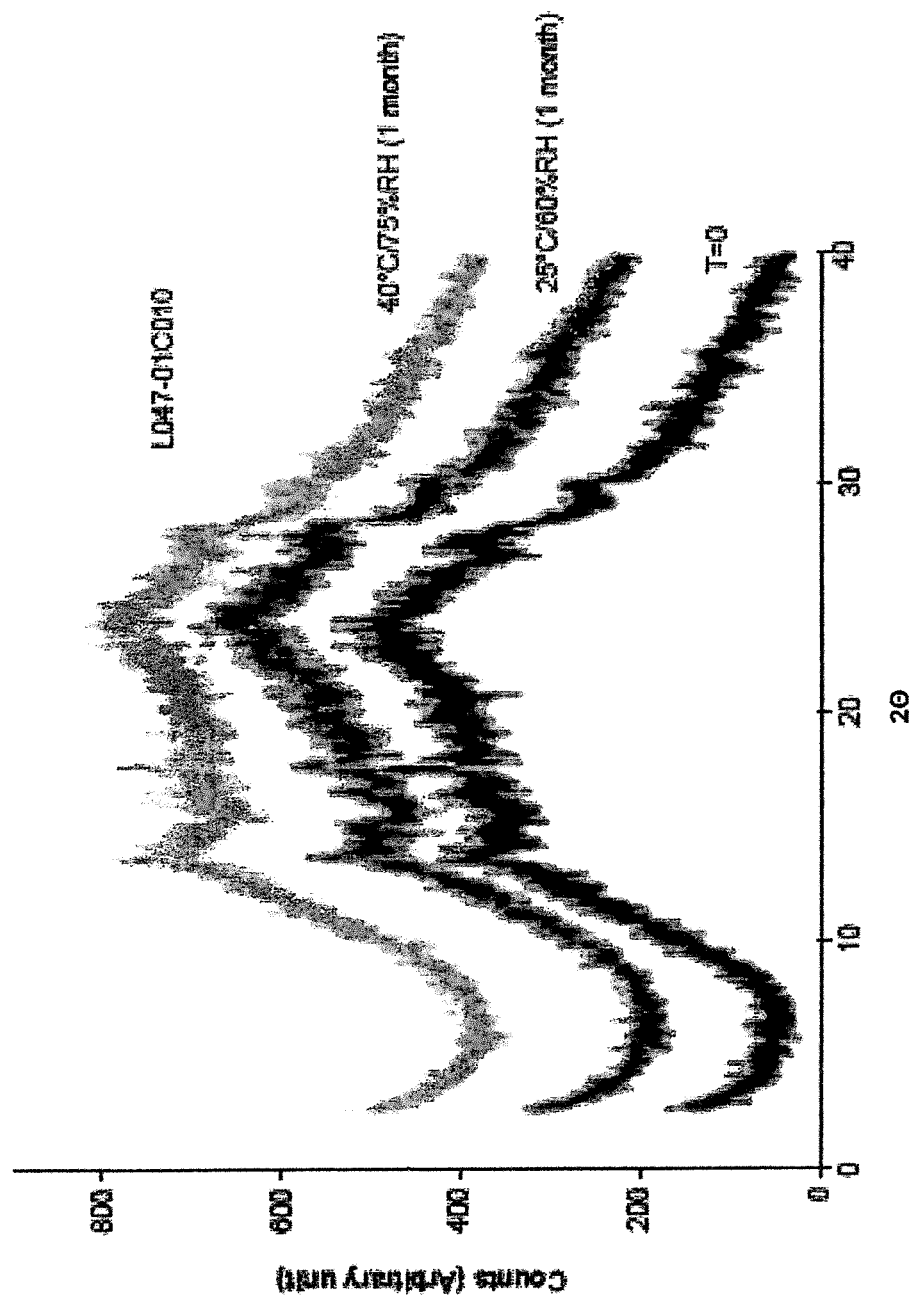

FIG. 15 shows XRPD diffractograms for Lot C010 at T=0 (black trace) after 1 month at 25° C./60% RH (red trace) and after 1 month at 40° C./75% RH (green trace).

Figure 16:
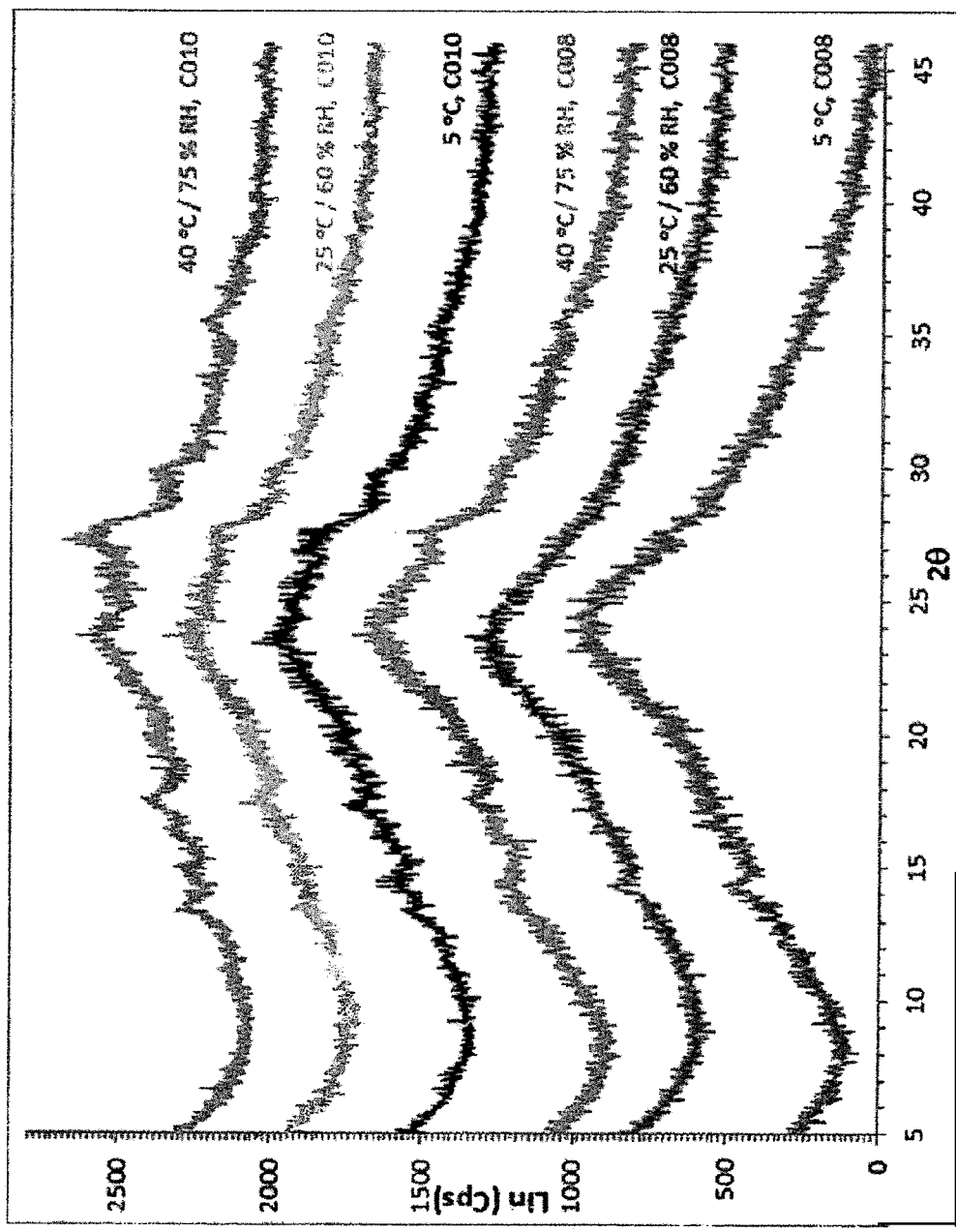
Figure 17:
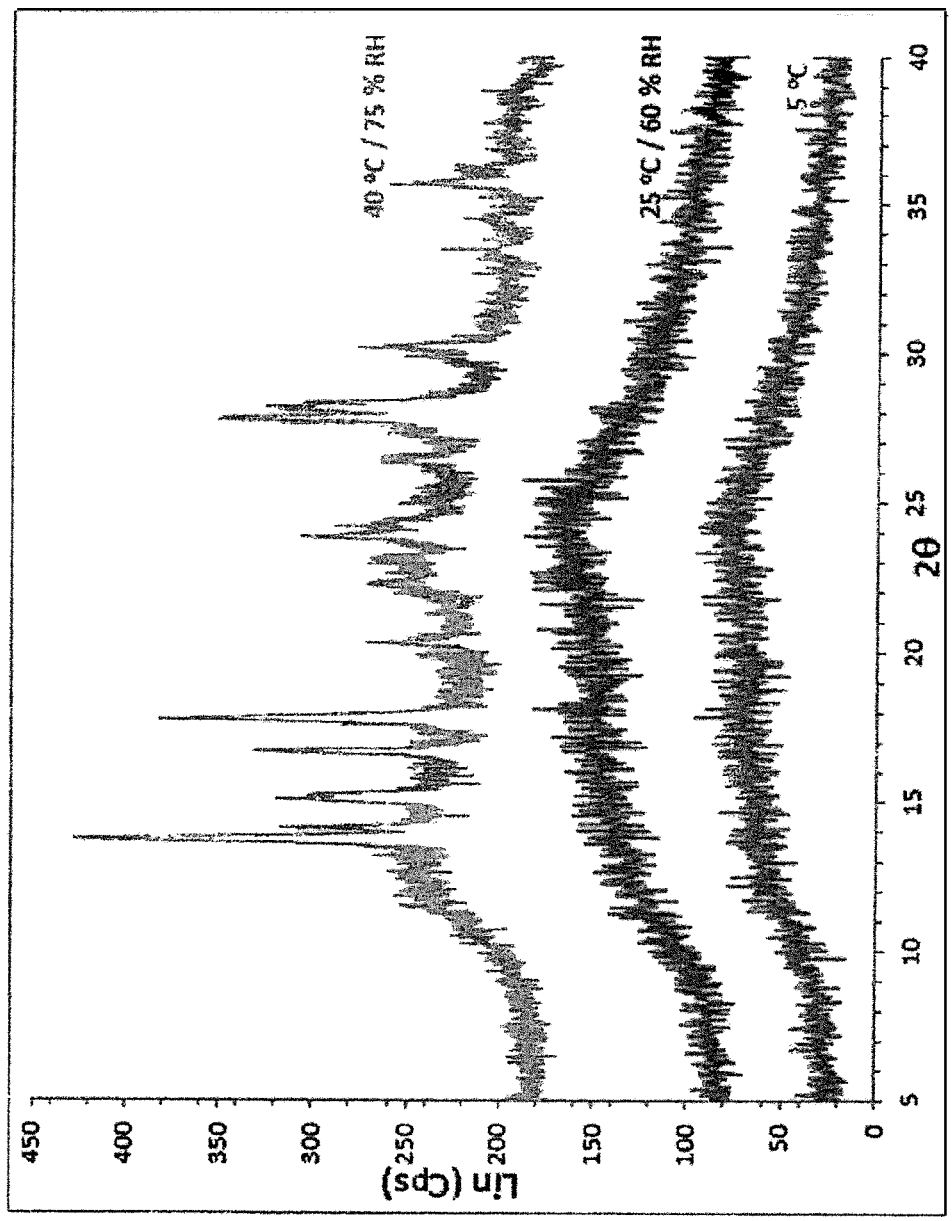

FIG. 16 shows XRPD diffractograms for Lots C008 and C010 after 3 months stability storage FIG. 17 shows XRPD diffractograms for Lot C008 after 6 months stability storage In the Examples, the following abbreviations are used:
API Active pharmaceutical ingredient
DCM dichloromethane
DMSO N,N-dimethylsulfoxide
HPMC hydroxypropylmethylcellulose
HPβCD 2-hydroxypropyl-β-cyclodextrin
HPMCAS Hypromellose-Acetate-Succinate
MCC Microcrystalline cellulose
MeOH methanol
NaOH sodium hydroxide
ND Not determined
N/De Not detected
NL/h normal liter/hour
NT Not tested
PVP polyvinylpyrrolidone
RH Relative humidity
RRT Relative retention time
RT Room temperature
SDI Spray-dry Intermediates (i.e. spray dried compositions which can be used to prepare pharmaceutical formulations).
SGF Simulated gastric fluid (US Pharmacopeia)
SIF Simulated intestinal fluid (US Pharmacopeia)

Kollidon® VA 64 is a polyvinylpyrrolidone/vinyl acetate copolymer supplied by BASF.

In the Examples, the following methods were used.

X-Ray Diffraction

The crystal structure of the compound was studied by X-Ray Powder Diffraction (XRPD) using a Siemens D-5000 X-ray diffractometer with Co Kα radiation (λ=1.7890 Å) at a scanning speed of 0.02° 2θ s$^{-1}$ with a 1 s step time over a range of 2-40° 2θ. Diffractograms in FIG. 16 were done using a Phillips X'PERT with Cu αK radiation (λ=1.54056 Å) at a scan speed of 0.02° s$^{-1}$ 2θ over a range of 5-46° 2θ.

HPLC Methods

| Parameters | Analytical Method | Dissolution Method* |
|---|---|---|
| Column | Waters Symmetry Shield RP8, 150 × 3.9 mm, 5 µm | |
| Column Temperature | 40° C. | |
| Tray Temperature | 20° C. | |
| Injection Volume | 5 µL | |
| Detector Wavelength | 229 nm | |
| Mobile Phase A (MPA) | TEAP†:Acetonitrile (80:20 by vol) | |
| Mobile Phase B (MPB) | TEAP†:Acetonitrile (20:80 by vol) | |
| Elution | Gradient | Isocratic 80% MPA/ 20% MPB |

| | Time (min.) | MPA (%) | MPB (%) | |
|---|---|---|---|---|
| Gradient | 0.0 | 100 | 0 | N/A |
| | 10.0 | 100 | 0 | |
| | 45.0 | 33 | 67 | |
| | 50.0 | 12 | 88 | |
| | 51.0 | 0 | 100 | |
| | 55.0 | 0 | 100 | |
| | 56.0 | 100 | 0 | |
| | 60.0 | 100 | 0 | |

| | | |
|---|---|---|
| Flow Rate | 1.0 mL/min | |
| Run Time | 60 minutes | 7 minutes |
| Retention Time | ~20 minutes | ~4 minutes |
| Sample Diluent | NH$_4$HCO$_3$ (10 mM) in Acetonitrile:water (70:30 by vol) | |

*Used for solubilization studies (FIGS. 11 and 12)
†0.1% (v/v) orthophosphoric acid adjusted to pH 6.5 with triethylamine

EXAMPLE 1

Preparation of (5-Fluoro-2-methyl-3-quinolin-2-ylmethyl-indol-1-yl)-acetic acid (Compound 1)

Compound 1 was prepared according to a method similar to that set out in WO-A-2006/092579. The method for synthesis can be summarised in Scheme 1 and Step 2 may be carried out according to the process described in UK Patent Application No. 1121557.1, filed 15 Dec. 2011.

Scheme 1

Step 1

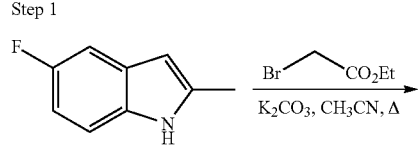

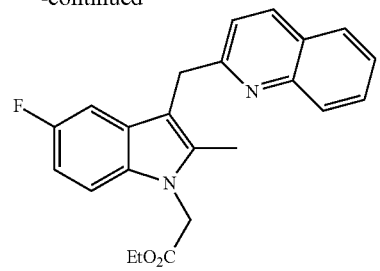

(5-fluoro-2-methyl-3-quinolin-2-yl methyl-indol-1-yl) acetic acid ethyl ester

Step 2

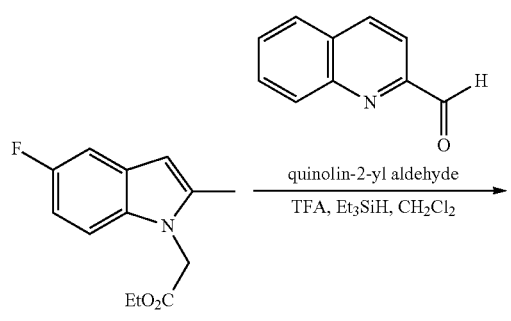

(5-fluoro-2-methyl-indol-1-yl) acetic acid ethyl ester

Step 3

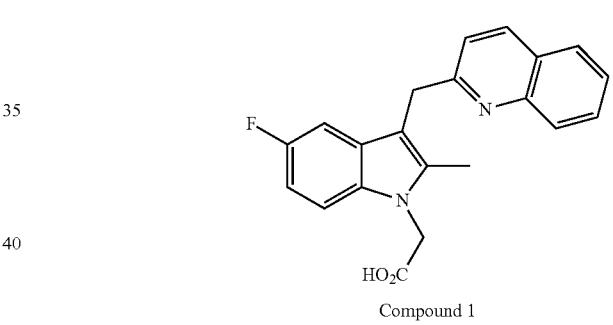

Compound 1

|  | Step 2 | Step 3 |
|---|---|---|
| Reagent and Conditions | (5-Fluoro-2-methyl-indol-1-yl)-acetic acid ethyl ester (736 mg; 1 equivalent) Quinolin-2-yl-aldehyde (502 mg; 1 equivalent) Triethylsilane (2.5 ml; 5 equivalents) Trifluoroacetic acid (0.7 ml; 2.9 equivalents) Dichloromethane (50 ml) 0° C. then allowed to warm to room temperature over 2 hours and stirred overnight 729 mg of product (62% yield) of product after chromatography | (5-Fluoro-2-methyl-3-quinolin-2-ylmethyl-indol-1-yl)-acetic acid ethyl ester (444 mg; 1 equivalent) Lithium hydroxide (199.5 mg; 4 equivalents) Tetrahydrofuran:water (100 ml; 1:1) 1 hour at room temperature 95% yield of product after concentration |

EXAMPLE 2

Solubility Screening

Before carrying out spray drying experiments, a solvent screening was performed to determine potential solvent that will allow sufficient concentration of Compound 1 in spray drying solution. Approximately 50 mg of Compound 1 was added to 100 mL of each evaluated solvent until visual observation of solution saturation. Solutions were kept in closed container for 12 h at room temperature under continuous stirring. The results are shown in Table 1.

TABLE 1

| Solvent | Compound 1 Solubility (g/L) |
|---|---|
| Purified water | <0.5 |
| Chloroform | <0.5 |
| Dichloromethane (DCM) | <0.5 |
| Carbon tetrachloride | <0.5 |
| Toluene | <0.5 |
| Tween 80 (1% v/v) | <0.5 |
| Span 80 (1% v/v) | <0.5 |
| Sodium dodecyl sulfate (2% w/v) | <0.5 |
| Hexadecyltrimethylammonium (0.05% w/v) | <0.5 |
| Tris(hydroxymethyl) aminoethane (1% w/v) | <0.5 |
| Dimethyl sulfoxide (DMSO) | 5.5-6.0 |
| DMSO/DCM (75/25 v/v) | 2.5-3.0 |
| DMSO/DCM (50/50 v/v) | 1.0-1.5 |
| DMSO/$H_2O$ (75/25 v/v) | 2.0-2.5 |
| DMSO/$H_2O$ (50/50 v/v) | <0.5 |
| DMSO/Ethanol (75/25 v/v) | 0.5-1.0 |
| DMSO/Ethanol (50/50 v/v) | 0.5-1.0 |
| Sodium hydroxide 0.5N | >90 (at 45° C.) |

The results of the solubility screening show that Compound 1 is particularly soluble in sodium hydroxide. However, this high solubility is believed to occur because in sodium hydroxide, Compound 1 is converted to its sodium salt. The solution containing 90 g/L of Compound 1 was cooled down to room temperature which resulted in the formation of a solid precipitate. This precipitate was filtered and washed 5 times with cold water (1-2° C.). The solid was dried for 36 h at 45° C. under vacuum (−15 mm Hg) and the dry cake was ground with a mortar/pestle and sieved through a 50 mesh screen. The material was identified as the sodium salt of Compound 1.

Apart from sodium hydroxide, the solvent in which Compound 1 is most soluble is DMSO and this is also a suitable solvent for Compound 1. Thus, according to solvent screening results (Table 1), DMSO and sodium hydroxide were selected as solvent for the spray drying of Compound 1.

COMPARATIVE EXAMPLE 3

Spray Drying of Compound 1

COMPARATIVE EXAMPLE 3A

Spray Drying of Compound 1 in DMSO (Lot 001)

1 g of Compound 1 was dissolved in 200 mL of DMSO. The solution was spray-dried using a Mini Spray Dryer model B-290 (Buchi, Zurich, Switzerland) with the following operating parameters: 1.5 mm nozzle; 3.8±0.1 mL/min spray rate; 220±4° C. inlet temperature; 120±3° C. outlet temperature; 550±20 NL/h atomization flow, and 90% air flow (~35 m³/h). Under these conditions, 311 mg of spray-dried material was collected (yield=31%).

COMPARATIVE EXAMPLE 3B

Spray Drying of Compound 1 in Sodium Hydroxide (Lot 002)

1.74 g of Compound 1 was dissolved in 100 mL of 0.05N NaOH (17.4 g/L) (molar ratio Compound 1:NaOH, 1:1) by heating the solution at 45° C. The solution was cool down to room temperature and the solution was spray dried using the Buchi B-290 with the following operating parameters: 1.5 mm nozzle; 3.3±0.1 mL/min spray rate; 140±2° C. inlet temperature; 71±1° C. outlet temperature; 350±20 NL/h atomization flow, and 95% air flow (~37 m³/h). Under these conditions, 1.066 g of spray dried material was collected (yield=61%).

COMPARATIVE EXAMPLE 3C

Spray Drying of Compound 1 in DMSO (Lot 017)

0.25 g of Compound 1 was dissolved in 500 mL of DMSO. The solution was spray-dried using a Mini Spray Dryer model B-290 (Buchi, Zurich, Switzerland) using compressed air as the drying gas, and with the following operating parameters: 1.5 mm nozzle; 4.0±0.1 mL/min spray rate (feed rate); 210±7° C. inlet temperature; 119±3° C. outlet temperature; 473 NL/h atomization flow, and 90% air flow (~35 m³/h). Under these conditions, 86.5 mg of spray dried material was collected (yield=35%).

COMPARATIVE EXAMPLE 4

Hot-Melt Dispersions in Hydrophilic Polymers

COMPARATIVE EXAMPLE 4A

Lot 003

Compound 1 (0.4 g)/Kollidon VA 64 (BASF, lot: 43962047G0) (1.6 g) solid dispersion was prepared by physical mixture. The mixture was melted using an open aluminum pan (30 mL). The mixture was kept at a temperature of 60-70° C. for 30 minutes. After solidification at RT, the resulting material was ground using mortar/pestle and passed through a 40 mesh screen to form granules.

COMPARATIVE EXAMPLE 4B

Lot 006

Compound 1 (0.2 g)/Kollidon VA 64 (BASF, lot: 43962047G0) (1.8 g) solid dispersion was prepared by physical mixture. The mixture was melted using an open aluminum pan (30 mL). The mixture was kept at a temperature of 60-70° C. for 30 minutes. The mixture was cooled down to room temperature. The resulting material was ground using mortar/pestle and passed through a 40 mesh screen to form granules.

COMPARATIVE EXAMPLE 4C

Lot 007

Compound 1 (0.4 g)/Hypromellose acetate succinate (HPMCAS) (Biddle Sawyer Corp, lot: 6093192) solid dispersion was prepared by physical mixture. The mixture was melted using an open aluminum pan (30 mL). The mixture was kept at a temperature of 50-60° C. for 30 minutes. The mixture was cooled down to room temperature. The resulting material was crushed using mortar/pestle and passed through a 40 mesh screen to form granules.

COMPARATIVE EXAMPLE 5

Solid Dispersions of Compound 1 in Gelucire

COMPARATIVE EXAMPLE 5A

Lot 004

Compound 1 (0.4 g) was dispersed in the melted Gelucire 44/14 (Gattefossé, lot: 115489) (1.6 g). The mixture was kept under stirring for 30 minutes at a temperature of 60° C. using a water-bath.

COMPARATIVE EXAMPLE 5B

Lot 005

Compound 1 (0.1 g) was dispersed in the melted Gelucire 44/14 (Gattefossé, lot: 115489) (1.4 g) containing Polyethylene Glycol 400 (PEG 400) (A&C, lot: TL0801AAJC/78022/02M02CA) (0.5 g). The mixture was kept under stirring for 30 minutes at a temperature of 60° C. using a water-bath.

COMPARATIVE EXAMPLE 5C

Lot 008

Compound 1 (0.2 g) was dispersed in the melted Gelucire 44/14 (Gattefossé, lot: 115489) (1.7 g) containing Sodium Lauryl Sulphate (SLS) (BioShop, lot 7M6316) (0.1 g). The mixture was kept under stirring for 30 minutes at a temperature of 60° C. using a water-bath.

COMPARATIVE EXAMPLE 5D

Lot 009

Compound 1 (0.2 g) was dispersed in the melted Gelucire 44/14 (Gattefossé, lot: 115489) (1.7 g) containing Poloxamer 407 (BASF, lot: WO40222) (0.1 g). The mixture was kept under stirring for 30 minutes at a temperature of 60° C. using a water-bath.

COMPARATIVE EXAMPLE 5E

Lot 010

Compound 1 (0.05 g) was dispersed in the melted Gelucire 44/14 (Gattefossé, lot: 115489) (1.4 g) containing Polyethylene Glycol 400 (PEG 400) (A&C, lot: TL0801AAJC/78022/02M02CA) (0.55 g). The mixture was kept under stirring for 30 minutes at a temperature of 60° C. using a water-bath.

COMPARATIVE EXAMPLE 5F

Lot 011

Compound 1 (0.05 g) was dispersed in the melted Gelucire 44/14 (Gattefossé, lot: 115489) (0.99 g) containing Polyethylene Glycol 200 (PEG 200) (A&C, lot: 20700603) (0.94 g) and 0.02 g of SLS (BioShop, lot 7M6316). The mixture was kept under stirring for 30 minutes at a temperature of 60° C. using a water-bath.

COMPARATIVE EXAMPLE 5G

Lot 0012

Compound 1 (0.2 g) was dispersed in the melted Gelucire 50/13 (Gattefossé, lot: 104818) (3.8 g). The mixture was kept under stirring for 30 minutes at a temperature of 60° C. using a water-bath.

COMPARATIVE EXAMPLE 5H

Lot 013

Compound 1 (0.18 g) was dispersed in the melted Gelucire 50/13 (Gattefossé, lot: 104818) (1.66 g) containing Poloxamer 407 (BASF, lot: WO40222) (0.16 g). The mixture was kept under stirring for 30 minutes at a temperature of 60° C. using a water-bath.

COMPARATIVE EXAMPLE 5I

Lot 024

Compound 1 (2.0 g) was dispersed in the melted Gelucire 44/14 (Gattefossé, lot: 115489) (8.0 g). The mixture was kept under stirring for 30 minutes at a temperature of 60-80° C. Hot melt formulation was encapsulated in size "1" white opaque hard gelatin capsules (Capsugel, lot: 70292091) for an equivalent of 100 mg of Compound 1/capsule.

COMPARATIVE EXAMPLE 5J

Lot 025

Compound 1 (2.0 g) was dispersed in the melted Gelucire 44/14 (Gattefossé, lot: 115489) (7.88 g) containing SLS (BioShop, lot 7M6316) (0.12 g). The mixture was kept under stirring for 30 minutes at a temperature of 60-80° C. Hot melt formulation was encapsulated in size "1" white opaque hard gelatin capsules (Capsugel, lot: 70292091) for an equivalent of 100 mg of Compound 1/capsule.

COMPARATIVE EXAMPLE 5K

Lot 026

Compound 1 (2.0 g) was dispersed in the melted Gelucire 44/14 (Gattefossé, lot: 115489) (7.88 g) containing Poloxamer 407 (BASF, lot: WO40222) (0.12 g). The mixture was kept under stirring for 30 minutes at a temperature of 60-80° C. Hot melt formulation was encapsulated in size "1" white opaque hard gelatin capsules (Capsugel, lot: 70292091) for an equivalent of 100 mg of Compound 1/capsule.

COMPARATIVE EXAMPLE 5L

Lot 027

Compound 1 (2.0 g) was dispersed in the melted Gelucire 44/14 (Gattefossé, lot: 115489) (5.0 g) containing PEG 400 (A&C, lot: TL0801AAJC/78022/02M02CA) (3.0 g). The mixture was kept under stirring for 30 minutes at a temperature of 60-80° C. Hot melt formulation was encapsulated in size "1" white opaque hard gelatin capsules (Capsugel, lot: 70292091) for an equivalent of 100 mg of Compound 1/capsule.

COMPARATIVE EXAMPLE 5M

Lot 034

Compound 1 (6.07 g) was dispersed in the melted Gelucire 44/14 (Gattefossé, lot: 115489) (14.70 g) containing PEG 400 (A&C, lot: TL0801AAJC/78022/02M02CA) (8.94 g) and SLS (BioShop, lot 9E11662) (0.30 g). The mixture was kept under stirring for 30 minutes at a temperature of 60-80° C. Hot melt formulation was encapsulated in size "1" white opaque hard gelatin capsules (Capsugel, lot: 70292091) for an equivalent of 100 mg of Compound 1/capsule.

EXAMPLE 6

Solid Dispersions of Compound 1

During the preparation of all batches, Compound 1 was first sieved with a 60 mesh (250 μm) sieve.

EXAMPLE 6A

Solid Dispersion in HPMC by Physical Mixture (Lot 014)

The Compound 1/HPMC solid dispersion was prepared by physical mixture and solvent evaporation. 0.9 g of HPMC E5 (low viscosity grade) (Dow, lot: TL08012407 (014-1 and 014-2) and UF16012412 (014-3)) was dissolved in 10 mL of methanol (MeOH)/dichloromethane (DCM) (50/50 v/v) under stirring at room temperature (RT). 0.1 g of Compound 1 was added to the polymeric solution. After API addition, 3 mL of dimethyl sulfoxide (DMSO) were added and the suspension was stirred for 30 minutes (014-1 and 014-2) and 1 hour (014-3) at RT. The mixture was prepared in transparent glass bottle and stirred with a magnetic stir. The solvent was evaporated as follows:

- lot 014-1: by direct heating;
- lot 014-2: using a water-bath at 100° C. with an air jet for a period of time of 7 hours and under stirring;
- lot 014-3A: using a water-bath at 100° C. during approximately 1.5 hours under stirring and 64 hours in a vacuum system (a small desiccators containing anhydrous calcium sulfate) placed into the oven at 50° C.;
- lot 014-3B: using a water-bath at 100° C. during approximately 1.5 hours under stirring and 64 hours in the fume hood at RT;
- lot 014-3C: using a water-bath at 100° C. during approximately 1.5 hours under stirring and 64 hours in the fume hood at RT. After, 5 mL of MeOH were added and the sample was dried under air jet until total solvent evaporation.

EXAMPLE 6B-1

Solid Dispersion in HPMC by Spray-Drying (Lot 015-1)

The solution was prepared as lot 014. 9.0 g of HPMC E5 (low viscosity grade) (Dow, lot: UF16012412) were dissolved in 100 mL of MeOH/DCM (50/50 v/v) under stirring (38 minutes) at RT. Later, 30 mL of DMSO and 1.0 g of Compound 1 were added to the polymeric solution. The suspension was stirred for 1 hour at RT. The mixture was prepared in transparent glass bottle and stirred with a magnetic bar. Partial evaporation of the solvent was achieved by direct heating at a temperature of 70-90° C. until a clear solution was obtained (volume 50 mL). This solution was viscous at temperatures of 70-90° C. and formed a transparent gel at RT. Before the spray-drying process while maintaining the solution at the same temperature, 22 mL of MeOH/DCM (50/50 v/v) were added for total solids content in the spray drying solution of ~14% w/v. The addition of solvent was necessary in order to reduce the viscosity and to facilitate the spray-drying process. This solution was spray-dried using the Buchi B-290 with the following operating parameters: 1.5 mm nozzle; ~7.5 mL/min spray rate; 194±2° C. inlet temperature; 109±1° C. outlet temperature; 473 NL/h atomization flow, and 95% air flow (~37 m³/h).

EXAMPLE 6B-2

Solid Dispersion in HPMC by Spray-Drying (Lot 015-2)

The solution was prepared as lot 015. 9.0 g of HPMC E5 (low viscosity grade) (Dow, lot: UF16012412) were dissolved in 100 mL of MeOH/DCM (50/50 v/v) under stirring at RT. Later, 30 mL of DMSO and 1.0 g of Compound 1 were added to the polymeric solution. The suspension was stirred for 1 hour at RT. The mixture was prepared in transparent glass bottle and stirred with a magnetic bar. Partial evaporation of the solvent was achieved using a water-bath at 100° C. until a clear solution was obtained (volume 60 mL). The solution was viscous at temperatures of 70-90° C. and formed a transparent gel at RT. 1 hour later, the formed gel was heated using a water-bath at 100° C. and 115 mL of MeOH/DCM (50/50 v/v) were added for total solids content in the spray drying solution of ~5.7% w/v. The addition of solvent formed an opaque suspension. This suspension was transferred to an amber glass bottle and kept between 4-8° C. until spray-drying step. The suspension was spray-dried using the Buchi B-290 with the following operating parameters: 1.5 mm nozzle; ~3.9 mL/min spray rate; 169±2° C. inlet temperature; 96±3° C. outlet temperature; 473 NL/h atomization flow, and 95% air flow (~37 m³/h). The stirring was maintained during the spray-drying to avoid precipitation.

EXAMPLE 6B-3

Solid Dispersion in HPMC by Spray-Drying (Lot 015-3)

The solution was prepared as lot 015. 9.0 g of HPMC E5 (low viscosity grade) (Dow, lot: UF16012412) were dissolved in 100 mL of MeOH/DCM (50/50 v/v) under stirring at RT. Later, 30 mL of DMSO and 1.0 g of Compound 1 were added to the polymeric solution. The suspension was stirred for 1 hour at RT. The mixture was prepared in transparent glass bottle and stirred with a magnetic bar. Partial evaporation of the solvent was achieved using a water-bath at 100° C. until a clear solution was obtained (volume ~50 mL). The transparent solution was viscous at temperatures of 70-90° C. 50 mL of DMSO were added for total solids content in the spray drying solution of 10% w/v. The solution was maintained under stirring/heating and was spray-dried using the Buchi B-290 with the following operating parameters: 1.5 mm nozzle; ~4 mL/min spray rate; 212±2° C. inlet temperature; 106±5° C. outlet temperature; 473 NL/h atomization flow, and 95% air flow (~37 m³/h).

COMPARATIVE EXAMPLE 6C

Solid Dispersion in HPβCD by Physical Mixture (Lot 016)

The Compound 1/HPβCD solid dispersion was prepared by physical mixture and solvent evaporation. 0.9 g of HPβCD (Cavasol® W7 HP Pharma, ISP lot: 73Lot 024) were dissolved in 10 mL of MeOH/DCM (50/50 v/v) under stirring at RT. 0.1 g of Compound 1 was added to the solution. After API addition, 3 mL of DMSO were added and the suspension was stirred for 30 minutes at RT. The mixture was prepared in transparent glass bottles and stirred with magnetic bar. The solvent was evaporated as lot 014-3C but with the addition of 10 mL of MeOH, 24 h of drying were needed.

EXAMPLE 6D

Solid Dispersion in PVPK30 by Physical Mixture (Lot 018)

The Compound 1/PVPK30 solid dispersion was prepared by physical mixture and solvent evaporation. 0.9 g of PVPK30 (ISP, lot: 05700181648) were dissolved in 10 mL of methanol/dichloromethane (50/50 v/v) under stirring at RT. 0.1 g of Compound 1 was added to the solution. After API addition, 3 mL of DMSO were added and the suspension was stirred for 1 h at RT. The mixture was prepared in transparent glass bottles and stirred with magnetic bar. After partial evaporation of the solvents using a water-bath at 100° C., Compound 1 was completely dissolved (final volume ~5 mL). The solvent was evaporated as lot 014-3C.

EXAMPLE 6E

Solid Dispersion in PVPK30 by Spray-Drying (Lot 019)

The Compound 1/PVPK30 solid dispersion was prepared by physical mixture and solvent evaporation. 9.0 g of PVPK30 (ISP, lot: 05700181648) were dissolved in 100 mL of MeOH/DCM (50/50 v/v) under stirring at RT. 1.0 g of Compound 1 was added to the solution. After API addition, 30 mL of DMSO were added and the suspension was stirred for 1 h at RT. The solution was prepared in transparent glass bottles and stirred with magnetic bar. Partial evaporation of the solvent was achieved using a water-bath at 100° C. A transparent non viscous solution was obtained after 1 h55 min (final volume ~50 mL). The solution was cool down to room temperature and transferred to an amber glass bottle which was kept between 4-8° C. until spray-drying step. Before the spray-drying step, 50 mL of DMSO were added for total solids content in the spray drying solution of 10%. The solution was maintained under stirring/heating and was spray-dried using the Buchi B-290 with the following operating parameters: 1.5 mm nozzle; ~4 mL/min spray rate; 214±1° C. inlet temperature; 114±5° C. outlet temperature; 473 NL/h atomization flow, and 90% air flow (~35 m³/h).

EXAMPLE 6F-1

Solid Dispersion in HPMC by Spray-Drying (Lot 020-1)

6.0 g of HPMC E5 (Dow, lot: UF16012412) were dissolved in 100 mL of MeOH/DCM (50/50 v/v) under stirring at RT. Later, 30 mL of DMSO and 4.0 g of Compound 1 were added to the polymeric solution. The suspension was stirred for 1 h at RT. The mixture was prepared in transparent glass bottle and stirred with a magnetic bar. Partial evaporation of the solvent was achieved using by direct heating until a clear solution was obtained (volume 50 mL). The transparent solution was slightly viscous. 50 mL of DMSO were added for total solids content in the spray drying solution of 10%. The solution was maintained under stirring/heating and was spray-dried using the Buchi B-290 with the following operating parameters: 1.5 mm nozzle; ~5 mL/min spray rate; 200±2° C. inlet temperature; 110±3° C. outlet temperature; 473 NL/h atomization flow, and 95% air flow (~37 m³/h).

EXAMPLE 6F-2

Solid Dispersion in HPMC by Spray-Drying (Lot 020-2)

6.0 g of HPMC E5 (Dow, lot: UF16012412) were dissolved in 100 mL of MeOH/DCM (50/50 v/v) under stirring at RT. Later, 30 mL of DMSO and 4.0 g of Compound 1 were added to the polymeric solution. The suspension was stirred for 1 h at RT. The mixture was prepared in transparent glass bottle protected from light and stirred with a magnetic bar. Partial evaporation of the solvent was achieved using a water-bath at 100° C. When a volume of 50 mL was reached, the solution was directly heated under continuous stirring until a clear solution was obtained (5-7 minutes). The transparent solution was slightly viscous. 50 mL of DMSO were added for total solids content in the spray drying solution of 10%. The solution was directly spray-dried using the Buchi B-290 with the following operating parameters: 1.5 mm nozzle; 2.5 mL/min spray rate; 200±2° C. inlet temperature; 106±3° C. outlet temperature; 473 NL/h atomization flow, and 90% air flow (~35 m³/h).

EXAMPLE 6G-1

Solid Dispersion in PVPK30 by Spray-Drying (Lot 021-1)

6.0 g of PVPK30 (ISP, lot: 05700181648) were dissolved in 100 mL of MeOH/DCM (50/50 v/v) under stirring at RT. Later, 30 mL of DMSO and 4.0 g of Compound 1 were added to the polymeric solution. The suspension was stirred for 1 h at RT. The mixture was prepared in transparent glass bottle and stirred with a magnetic bar. Partial evaporation of the solvent was achieved using by direct heating until a clear solution was obtained (volume 50 mL). The transparent solution was non-viscous. 50 mL of DMSO were added for total solids content in the spray drying solution of 10%. This solution was directly introduced into the spray-drier and spray-dried using the following operating parameters: 1.5 mm nozzle; ~4 mL/min spray rate; 200±2° C. inlet temperature; 94±1° C. outlet temperature; 473 NL/h atomization flow, and 90% air flow (~35 m³/h).

EXAMPLE 6G-2

Solid Dispersion in PVPK30 by Spray-Drying (Lot 021-2)

6.0 g of PVPK30 (ISP, lot: 05700181648) were dissolved in 100 mL of MeOH/DCM (50/50 v/v) under stirring at RT. Later, 30 mL of DMSO and 4.0 g of Compound 1 were added to the polymeric solution. The suspension was stirred for 1 h at RT. The mixture was prepared in transparent glass bottle protected from light and stirred with a magnetic bar. Partial evaporation of the solvent was achieved using a water-bath at 100° C. When a volume of 50 mL was reached, the solution was directly heated under continuous stirring until a clear solution was obtained (5-7 minutes). The transparent solution was non-viscous. 50 mL of DMSO were added for total solids content in the spray drying solution of 10%. No precipitation was observed after approximately 24 h at RT. This solution was directly introduced into the spray-drier and spray-dried using the following operating parameters: 1.5 mm nozzle; ~3 mL/min spray rate; 200±2° C. inlet temperature; 105±5° C. outlet temperature; 473 NL/h atomization flow, and 90% air flow (~35 m$^3$/h).

EXAMPLE 6H

Solid Dispersion in HPMC by Spray-Drying (Lot 022)

7.0 g of HPMC E5 (Dow, lot: UF16012412) were dissolved in 100 mL of MeOH/DCM (50/50 v/v) under stirring at RT. Later, 30 mL of DMSO and 3.0 g of Compound 1 were added to the polymeric solution. The suspension was stirred for 1 h at RT. The mixture was prepared in transparent glass bottle protected from light and stirred with a magnetic bar. Partial evaporation of the solvent was achieved using a water-bath at 100° C. When a volume of 50 mL was reached, the solution was directly heated under continuous stirring until a clear solution was obtained (5-7 minutes). The transparent solution was slightly viscous. 50 mL of DMSO were added for total solids content in the spray drying solution of 10%. After approximately 24 h at RT a slight precipitation was observed. When this solution was placed in the water-batch for a few minutes, the precipitate disappeared and no precipitation was observed again. The solution was directly introduced into the spray-drier and spray-dried using the following operating parameters: 1.5 mm nozzle; ~3 mL/min spray rate; 202±2° C. inlet temperature; 102±2° C. outlet temperature; 473 NL/h atomization flow, and 90% air flow (~35 m$^3$/h).

EXAMPLE 6H

Solid Dispersion in PVPK30 by Spray-Drying (Lot 023)

7.0 g of PVPK30 (ISP, lot: 05700181648) were dissolved in 100 mL of MeOH/DCM (50/50 v/v) under stirring at RT. Later, 30 mL of DMSO and 3.0 g of Compound 1 were added to the polymeric solution. The suspension was stirred for 1 h at RT. The mixture was prepared in transparent glass bottle protected from light and stirred with a magnetic bar. Partial evaporation of the solvent was achieved using a water-bath at 100° C. When a volume of 50 mL was reached, the solution was directly heated under continuous stirring until a clear solution was obtained (5-7 minutes). The transparent solution was non-viscous. 50 mL of DMSO were added for total solids content in the spray drying solution of 10%. The solution was introduced into the spray-drier and spray-dried using the following operating parameters: 1.5 mm nozzle; ~3 mL/min spray rate; 202±2° C. inlet temperature; 96±8° C. outlet temperature; 473 NL/h atomization flow, and 90% air flow (~35 m$^3$/h).

EXAMPLE 6J

Solid Dispersion in HPMC by Spray-Drying (Lot 028)

17.5 g of HPMC E5 (Dow, lot: UF16012412) were dissolved in 250 mL of MeOH/DCM (50/50 v/v) under stirring at RT. Later, 75 mL of DMSO and 7.5 g of Compound 1 were added to the polymeric solution. The suspension was stirred for 30 minutes at RT. The mixture was prepared in transparent glass bottle and stirred with a magnetic bar. Partial evaporation of the solvent was achieved by direct heating from 25° C. ($T_0$) to 109° C. ($T_{f(100\ min)}$) until approximately 120 mL of a clear solution was obtained (after 100 minutes of heating). After that the heating was stopped and 130 mL of DMSO were added for total solids content in the spray drying solution of 10%. This solution was directly introduced into the spray-drier and spray-dried using the following operating parameters: 1.5 mm nozzle; 4.0 mL/min spray rate; 210±1° C. inlet temperature; 112±7° C. outlet temperature; 473 NL/h atomization flow, and 90% air flow (~35 m$^3$/h). The product from the collection vessel (FIG. 1) was identified L028A and the product recovered from the cylinder (spray dry chamber) as L028B.

EXAMPLE 6K

Solid Dispersion in PVPK30 by Spray-Drying (Lot 029)

17.5 g of PVPK30 (ISP, lot: 05700181648) were dissolved in 250 mL of MeOH/DCM (50/50 v/v) under stirring at RT. Later, 75 mL of DMSO and 7.5 g of Compound 1 were added to the polymeric solution. The suspension was stirred for 30 minutes at RT. The mixture was prepared in transparent glass bottle and stirred with a magnetic bar. Partial evaporation of the solvent was achieved by direct heating from 25° C. ($T_0$) to 110° C. ($T_{f(66\ min)}$) until approximately 120 mL of a clear solution was obtained (after 66 minutes of heating). After that the heating was stopped and 130 mL of DMSO were added for total solids content in the spray drying solution of 10%. This solution was directly introduced into the spray-drier and spray-dried using the following operating parameters: 1.5 mm nozzle; 3.5 mL/min spray rate; 220±1° C. inlet temperature; 128±2° C. outlet temperature; 473 NL/h atomization flow, and 95-100% air flow (~38 m$^3$/h). The product from the collection vessel (FIG. 1) was identified L029A and the product recovered from the cylinder (spray dry chamber) as L029B.

EXAMPLE 6L

Solid Dispersion in HPMCAS by Spray-Drying (Lot 030)

7.0 g of Hypromellose-Acetate-Succinate LG grade (HPMCAS) (Shin-Etsu Chemical, lot: 8113240) were dissolved in 100 mL of MeOH/DCM (50/50 v/v) under stirring at RT. Later, 30 mL of DMSO and 3.0 g of Compound 1 were added to the polymeric solution. The suspension was stirred for 30 minutes at RT. The mixture was prepared in transparent glass bottle and stirred with a magnetic bar. Partial evaporation of the solvent was achieved by direct heating from 25° C. ($T_0$) to 119° C. ($T_{f(69\ min)}$) until approximately 50 mL of a clear solution was obtained (after 69 minutes of heating). After that the heating was stopped and 50 mL of DMSO were added for total solids content in the spray drying solution of 10%. This solution was directly introduced into the spray-drier and spray-dried using the following operating parameters: 1.5 mm nozzle; 2.5 mL/min spray rate; 219±2° C. inlet temperature; 120±3° C. outlet temperature; 473 NL/h atomization flow, and 95-100% air flow (~38 m$^3$/h). The product from the collection vessel (FIG. 1) was identified L030A and the product recovered from the cylinder (spray dry chamber) as L030B.

EXAMPLE 6M

Solid Dispersion in PVPK30 by Spray-Drying (Lot 031)

10.4 g of PVPK30 (ISP, lot: 05700181648) were dissolved in 130 mL of MeOH/DCM (50/50 v/v) under stirring at RT.

Later, 39 mL of DMSO and 2.6 g of Compound 1 were added to the polymeric solution. The suspension was stirred for 30 minutes at RT. The mixture was prepared in transparent glass bottle and stirred with a magnetic bar. Partial evaporation of the solvent was achieved by direct heating from 23° C. ($T_0$) to 113° C. ($T_{f(90\ min)}$) until approximately 65 mL of a clear solution was obtained (after 90 minutes of heating). After that the heating was stopped and 30 mL of DMSO and 60 mL of Acetone were added for total solids content in the spray drying solution of 8.4%. This solution was directly introduced into the spray-drier and spray-dried using the following operating parameters: 1.5 mm nozzle; 4.1 mL/min spray rate; 148±5° C. inlet temperature; 83±3° C. outlet temperature; 473 NL/h atomization flow, and 95% air flow (~37 m³/h).

EXAMPLE 6N

Solid Dispersion in HPMCE5 by Spray-Drying (Lot 032)

10.4 g of HPMC E5 (Dow, lot: UF16012412) were dissolved in 130 mL of MeOH/DCM (50/50 v/v) under stirring at RT. Later, 39 mL of DMSO and 2.6 g of Compound 1 were added to the polymeric solution. The suspension was stirred for 30 minutes at RT. The mixture was prepared in transparent glass bottle and stirred with a magnetic bar. Partial evaporation of the solvent was achieved by direct heating from 25° C. to 130° C. until approximately 65 mL of a clear solution was obtained (after 80 minutes of heating). After that the heating was stopped and 30 mL of DMSO and 60 mL of Acetone were added for total solids content in the spray drying solution of 8.4%. This solution was directly introduced into the spray-drier and spray-dried using the following operating parameters: 1.5 mm nozzle; 4.2 mL/min spray rate; 160±1° C. inlet temperature; 92±1° C. outlet temperature; 473 NL/h atomization flow, and 95% air flow (~37 m³/h).

EXAMPLE 6O

Solid Dispersion in PVPK30 by Spray-Drying (Lot 033)

19.95 g of PVPK30 (ISP, lot: 05700181648) were dissolved in 250 mL of MeOH/DCM (50/50 v/v) under stirring at RT. 5.06 g of Compound 1 were added to the polymeric solution. The suspension was stirred for 60 minutes at RT. 75 mL of DMSO were added under continuous stirring. The mixture was prepared in transparent glass bottle and stirred with a magnetic bar. Partial evaporation of the solvent was achieved by direct heating from 23° C. to 103° C. until approximately 110 mL of a clear solution was obtained (after 92 minutes of heating). After that, the heating was stopped and 25 mL of DMSO and 90 mL of Acetone were added for total solids content in the spray drying solution of 11%. This solution was directly introduced into the spray-drier and spray-dried using the following operating parameters: 1.5 mm nozzle; 4.6 mL/min spray rate; 159±4° C. inlet temperature; 97±2° C. outlet temperature; 473 NL/h atomization flow, and 95% air flow (~37 m³/h).

EXAMPLE 7

Crystal Structure Evaluation

Figure 1:
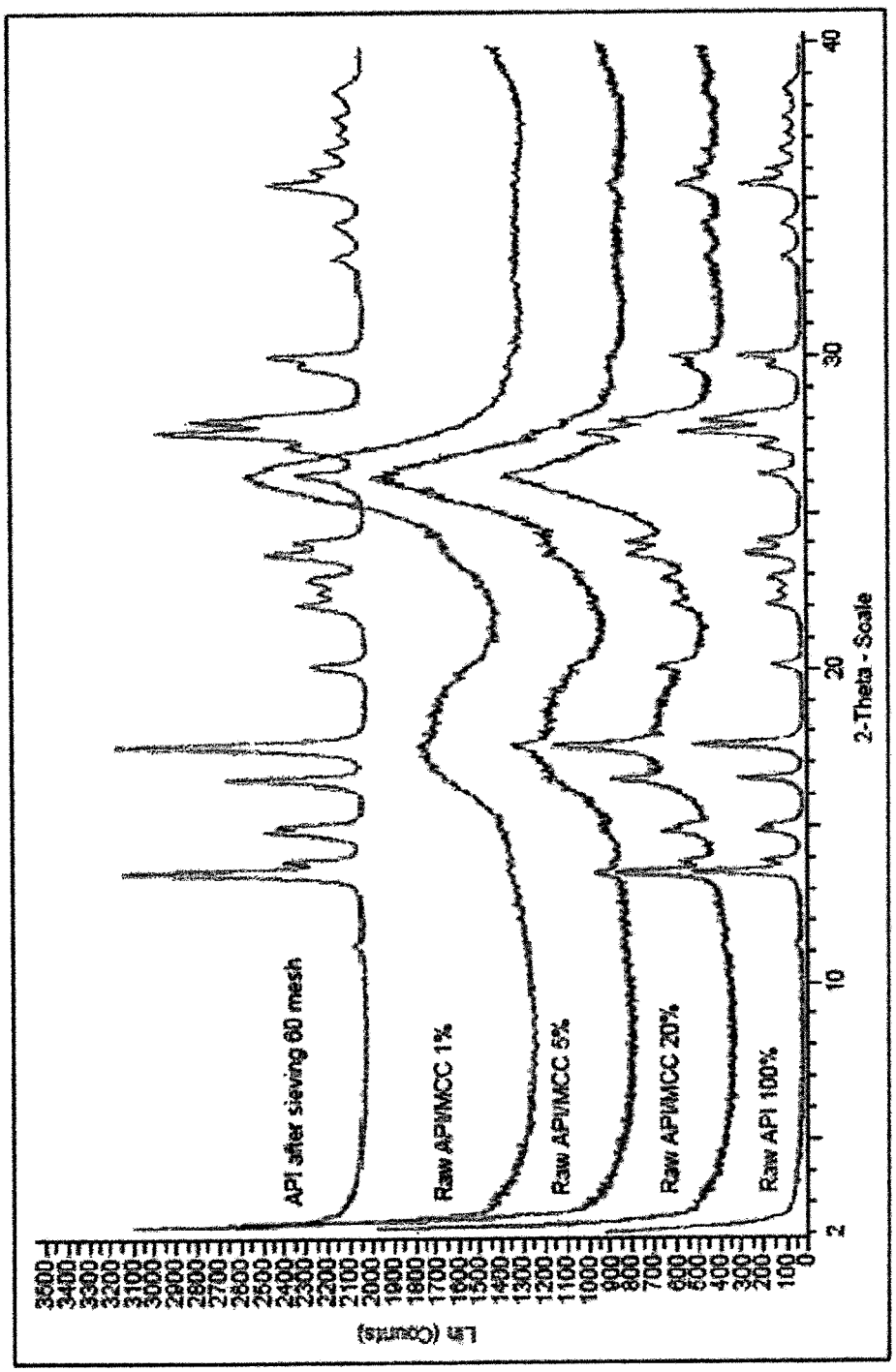
FIG. 1 shows XRPD patterns of Compound 1 as-received, after sieving through a 60 mesh sieve and blended with microcrystalline cellulose (MCC) (1, 5 and 20% Compound 1).

The sensitivity of the XRPD method was evaluated in a spiking experiment in which 1, 5 and 20% of Compound 1 was mixed with microcrystalline cellulose (MCC) (Avicel PH101, FMC, lot: P105815404) and the results are shown in FIG. 1. The XRPD diffractogram of 1, 5 and 20% Compound 1:MCC mixtures were compared to those of pure Compound 1 and mixtures of MCC and Compound 1. The X-ray diffraction of major crystalline peaks of Compound 1, situated at approximately 13.6 and 17.7° 2θ, can be observed in the X-ray diffraction pattern of the mixture containing 5% of crystalline Compound 1 which confirms that the XRPD limit of detection of crystalline Compound 1 is approximately 5% (FIG. 1).

The XRPD patterns of Compound 1 before and after the sieving step was identical (FIG. 1), indicating that sieving with a 60 mesh did not affect the crystal structure of this material.

The formulations tested by XRPD are summarized in Table 2. Except for sample 014-2, all the samples were analyzed immediately after preparation.

TABLE 2

| Lot ID (Example No.) | Ingredient | % w/w |
|---|---|---|
| 001, 017 (Comp. Ex. 3A, 3C) | OC000459 as-is | 100 |
| 002 (Comp. Ex. 3B) | OC000459 sodium salt | 100 |
| 003 (Comp. Ex. 4A) | OC000459:Kollidon VA 64 | 20:80 |
| 004 (Comp. Ex. 5A) | OC000459:Gelucire 44/14 | 20:80 |
| 005 (Comp. Ex. 5B) | OC000459:Gelucire 44/14:PEG 400 | 5:70:25 |
| 006 (Comp. Ex. 4B) | OC000459:Kollidon VA 64 | 10:90 |
| 007 (Comp. Ex. 4C) | OC000459:HPMCAS | 20:80 |
| 012 (Comp. Ex. 5G) | OC000459:Gelucire 50/13 | 5:95 |
| 014, 015 (Examples 6A, 6B) | OC000459:HPMC | 10:90 |
| 016 (Comp. Ex. 6C) | OC000459:HPβCD | 10:90 |
| 019 (Example 6E) | OC000459:PVPK30 | 10:90 |
| 020 (Example 6F) | OC000459:HPMC | 40:60 |
| 021 (Example 6G) | OC000459:PVPK30 | 40:60 |
| 022, 028 (Examples 6H, 6J) | OC000459:HPMC | 30:70 |
| 023, 029 (Examples 6I, 6K) | OC000459:PVPK30 | 30:70 |
| 027 (Comp. Ex. 5L) | OC000459:Gelucire 44/14:PEG 400 | 20:50:30 |
| 030 (Example 6L) | OC000459:HPMCAS | 30:70 |
| 031, 033 (Examples 6M, 6O) | OC000459:PVPK30 | 20:80 |
| 032 (Example 6N) | OC000459:HPMC | 20:80 |

FIGS. 1 to 5 show the distinct XRP diffractogram for the as-received and formulated samples of Compound 1.

Figure 2:
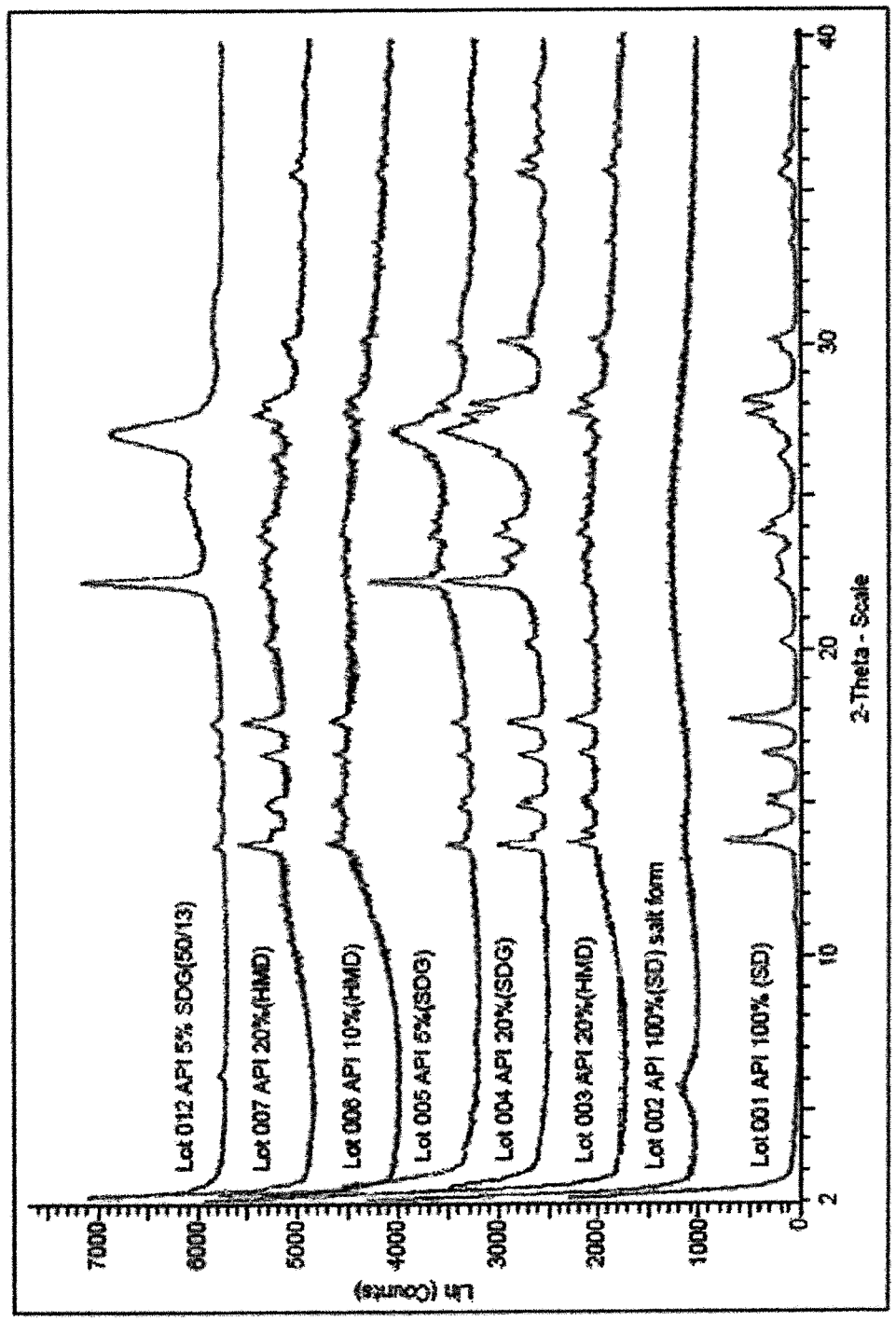
FIG. 2 shows XRPD patterns of Compound 1 in lots 001 to 007 and 012.
Figure 3:
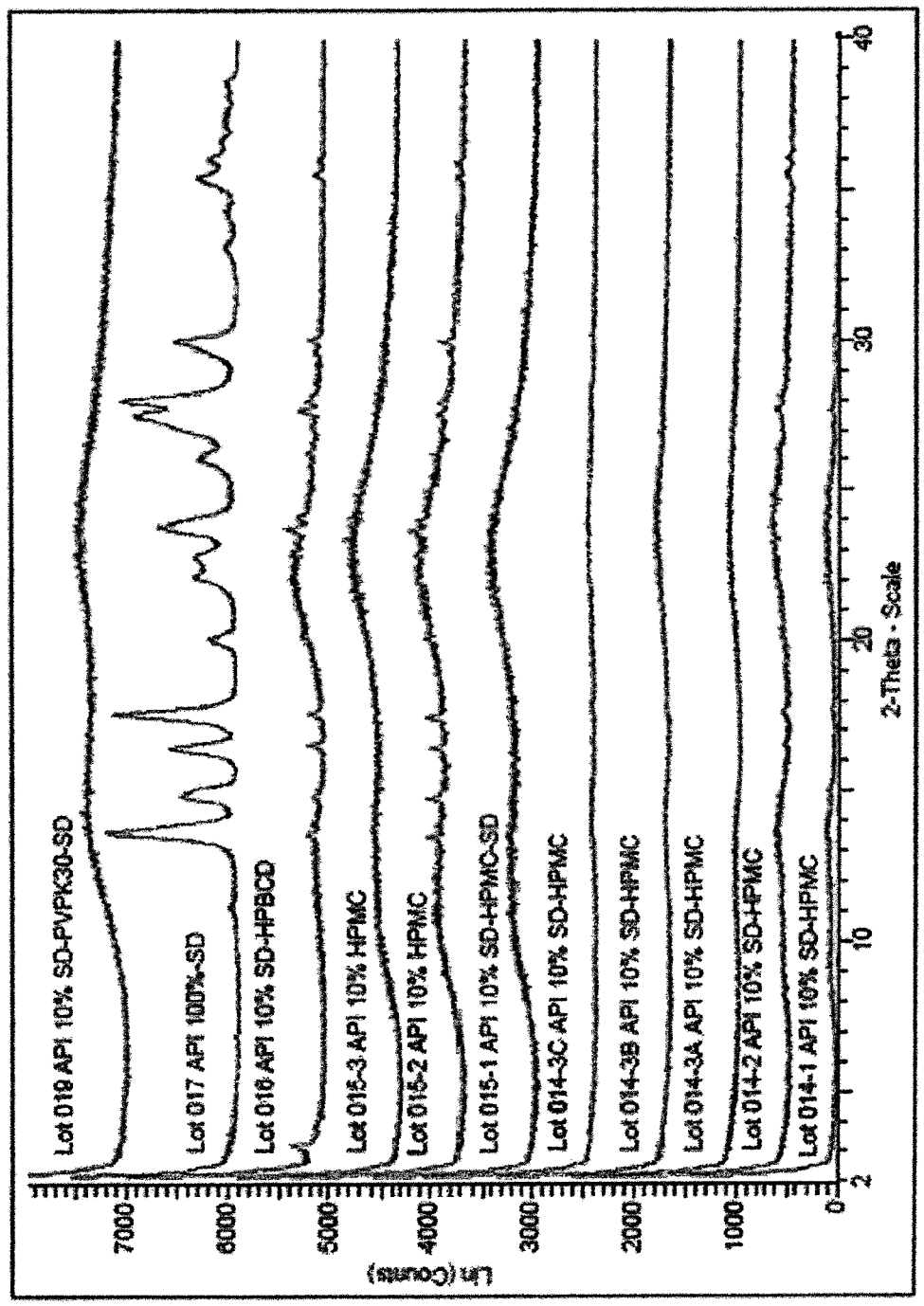
FIG. 3 shows XRPD patterns of Compound 1 in lots 014 to 017 and 019.
Figure 4:
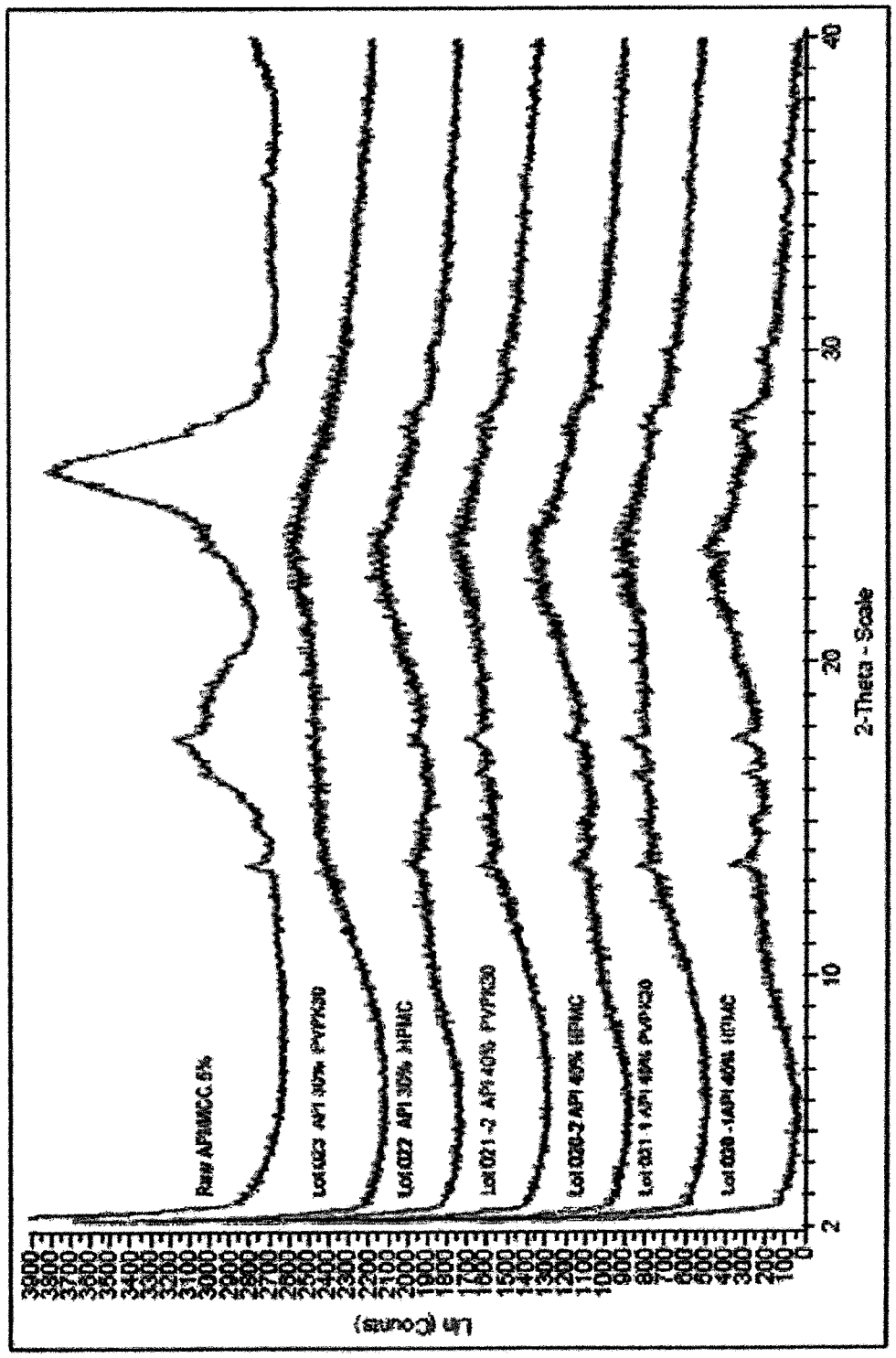
FIG. 4 shows XRPD patterns of Compound 1 in solid dispersion/spray drying lots 020 to 023.

As shown in FIG. 2, the crystalline structure of Compound 1 remained stable after spray-drying (lot 001) and dispersion in Gelucire 44/14 (lot 004) and Gelucire 50/13 (lot 012). However, an apparent increase of amorphous content was observed following the dispersion in PVP-VA (lots 003 and 006). Interestingly, a conversion into the amorphous form was observed for the spray-dried material dissolved using sodium hydroxide (lot 002).

XRPD data obtained for lot 014 (FIG. 3) also suggest that a solid dispersion of 10% API/90% HPMC after dissolution in DCM-MeOH-DMSO as solvent system resulted in drug amorphization. It was noted that DMSO solvent evaporation was a problem in the solid dispersion in HPMC (lot 014) and in PVPK30 (lot 018). Only sample 014-3C showed an appropriate drying of the material. Dispersion of 10% API in HPβCD (lot 016) only led to partial amorphization of Compound 1. In lot 018, DMSO could not be completely removed with the technique used and, consequently, this lot was not tested by XRPD.

The results obtained for lots 015 and 019 (FIG. 3) confirmed the amorphization of Compound 1 after solid dispersion/spray drying of this API (10%) in HPMC and in PVPK30 using DCM-MeOH-DMSO as solvent system. Solution from lots 015 and 019 became transparent with the final volume 50 mL where 1 g of API and 9 g of polymer were completely dissolved (20% w/v of solids). These solutions were viscous. In order to make a solution that was suitable for spray-drying, it was necessary to add more solvent to reduce the viscosity. In lot 015-1, 22 mL of MeOH/DCM (50/50 v/v) were added. When the solvent was added the tiny suspended particles were observed. This could be due to the HPMC. In lot 015-2, the addition of 115 mL of MeOH/DCM (50/50 v/v) resulted in a stable suspension (5.7% w/v of solids). This suspension was sprayed at RT under stirring. The solution from lot 015-3 resulted in a transparent slightly viscous liquid when 50 mL of DMSO were added. Solutions from lot 015-1 (14% w/v of solids) and 015-3 (10% w/v of solids) were kept under heating during the spray-drying. The solution from lot 019 resulted in a transparent non-viscous solution when 50 mL of DMSO were added (10% w/v of solids). This solution could be sprayed at RT and without agitation.

Under non-optimized conditions, the spray-drying yield of lots 015-2, 015-3 and 019 were 49, 59 and 65%, respectively. The percent yield refers to the percentage of the amounts recovered in the collection vessel from the amount of the solids dissolved. The preparation of the solution will be optimized in further studies to better define the operation parameters.

For the samples containing 40% of Compound 1 dispersed with HPMC and PVPK30 (lots 020 and 021 respectively), around 5% or less of the drug remains in the crystalline form the rest being in the amorphous state (FIG. 4). 30% of Compound 1 co-precipitated with PVP by spray-drying leads complete conversion into amorphous form (lot 023). However, using HPMC as polymer a very small quantity of the drug (probably less than 5%) remained crystalline (lot 022).

50-54% of spray-dried material from lots 020 to 023 was recovered in the collector. For lot 021-2 a yield of 72% was obtained. For these lots the powders were not sticky and showed an acceptable flowability. The PVP co-precipitates presented a finer particle size.

In agreement with previous XRPD studies, Compound 1 dispersed in Gelucire (lot 027) remained in the crystalline form (FIG. 5) even in the presence of PEG400.

Figure 5:
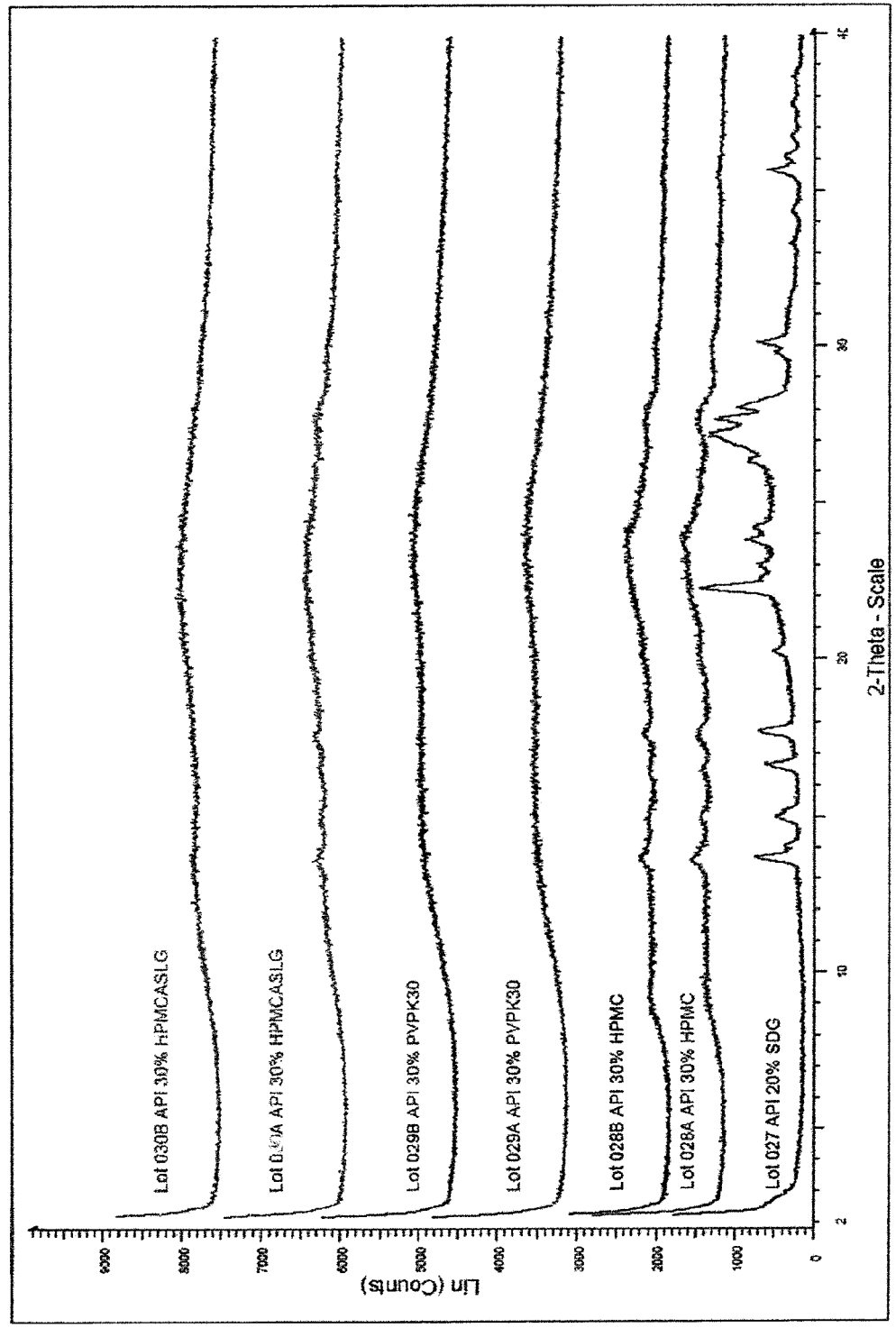
FIG. 5 shows XRPD patterns of Compound 1 in solid dispersion/spray drying lots 027 to 030.

For samples prepared by solid dispersion/spray drying with HPMC (lot 028) and with PVPK30 (lot 029) at a 30% drug load, the results were similar to those observed for lots 022 and 023 (FIG. 5). However, the intensity of the characteristic crystalline peaks at 2θ ~13.5, ~17.5 and ~27.5 decreases slightly for lot 028B compared with lot 028A. The major differences between 028A and 028B were the time of exposition to drying air (~210° C.) and the particle size, both were greater in lot 028B than 028A (product from the collection vessel). Increasing the stress and difference in crystal size can produce disorder in the corresponding crystal structure. The different crystal arrangements may lead to an infinite number of possible local amorphous structures.

The yield for lot 028 was 68% (46% of the amounts was recovered in the collection vessel), for lot 029 was 75% (61% in the collection vessel) and for lot 030 32% (11% in the collection vessel). Under these operating conditions the yield for lot 028 and 029 was improved but only 32% of the spray-dried material was recovered from lot 030. This was due to the sticking nature of HPMCAS under used conditions (DMSO as solvent and temperatures of 219±2° C.).

Figure 6:
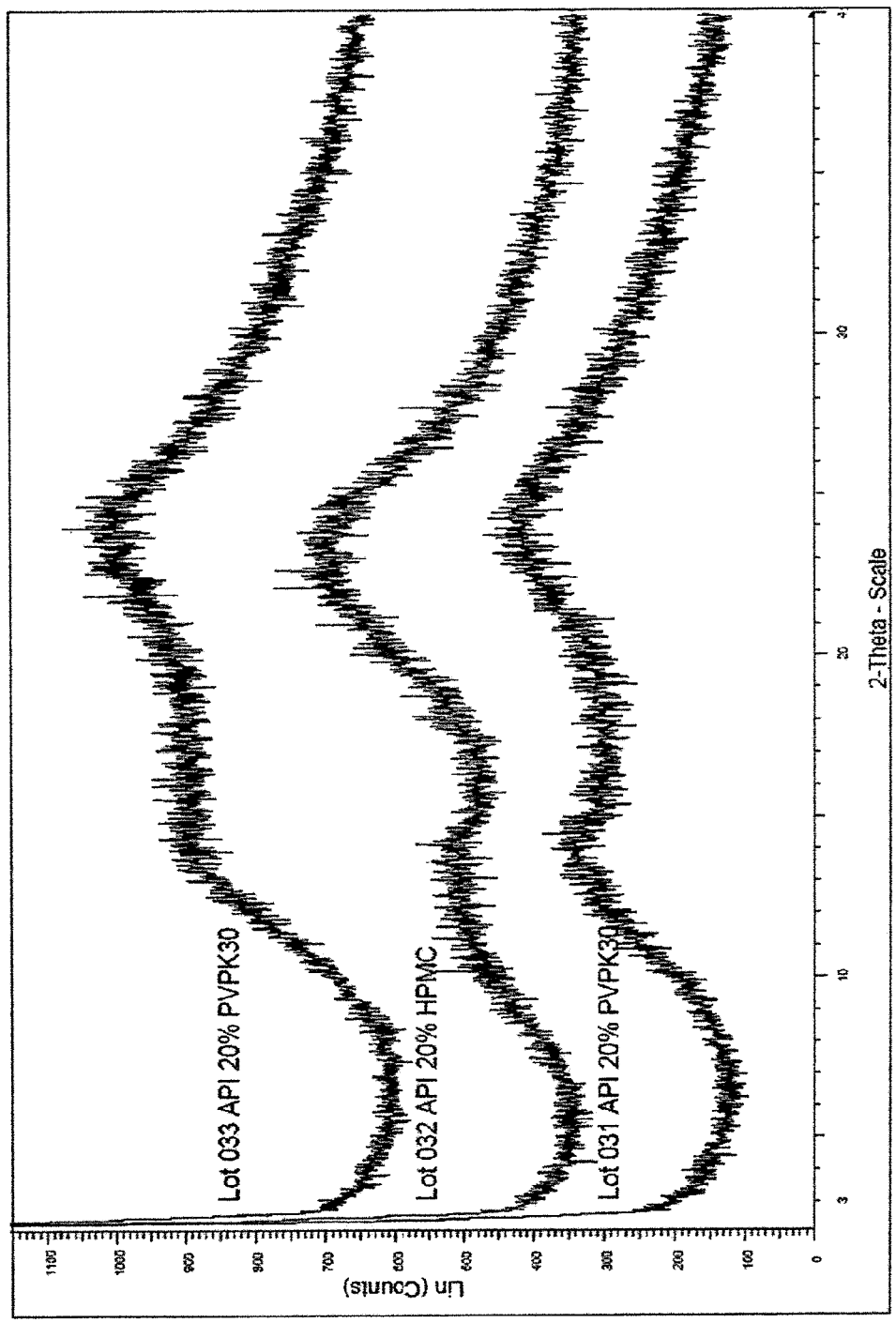
FIG. 6 shows XRPD patterns of Compound 1 in solid dispersion/spray drying lots 031 to 033.

For PVP (lots 031 and 033) and HPMC (lot 032) SDI (API 20%), a mixture of DMSO/acetone was used as solvent for the spray drying process. Therefore, the inlet temperature could be reduced from 220° C. to 150-160° C. These samples were also tested by XRPD measurement. Diffractograms can be found in FIG. 6. The results show that the lots containing 20% of API and prepared with a mixture of DMSO/Acetone were converted to the amorphous form. For these lots (031, 032 and 033), the spray drying yield was 65, 47 and 49%, respectively. During the spray-drying process of lots 032 and 033 an important amount of material accumulated in the dry chamber. This can probably be ascribed to problems during atomization. Indeed, the gas atomizing flow rate to the feed rate ratio influences the yield and the particle size. A lower ratio leads to wetting of the drying chamber by the sprayed droplets resulting in a lower yield. Also, when the atomizing flow rate is low, the drop exiting the nozzle tends to be greater so the resulting dried particle will be larger. In addition, the concentration of solids in the spray drying solution affects the particle size. Low solid concentration decreases the amount of solid in each droplet exiting the nozzle. Therefore, when the solvent in the droplet evaporates, a smaller particle remains. For lot 031 the total solids content in the spray drying solution was around 8% and 11% for lot 033.

To summarise, the lots having amorphous character were found to be lots 002 (Comparative Example 3B), 014 (Example 6A), 015 (Example 6B), 019-023 (Example 6E, Example 6F, Example 6G, Example 6H, Example 6I) and 028-033 (Example 6J, Example 6K, Example 6L, Example 6M, Example 6N, Example 6O). It is also probable that lot 018 (Example 6D) was an amorphous product but there were difficulties in removing the solvent.

The product of Comparative Example 3B was the sodium salt of Compound 1 rather than the free acid.

Therefore, amorphous Compound 1 was present in solid dispersions of the compound in:

| Lot | Ratio Compound 1:Polymer |
|---|---|
| HPMC: | |
| 014 | 10:90 |
| 015 | 10:90 |
| 020 | 40:60 |
| 022 | 30:70 |
| 028 | 30:70 |
| 032 | 20:80 |
| PVP | |
| 019 | 10:90 |
| 21 | 40:60 |
| 23 | 30:70 |
| 29 | 30:70 |
| 31 | 20:80 |
| 33 | 20:80 (approx.) |
| HPMCAS (lot 30). | |
| 030 | 30:70 |

EXAMPLE 8

Analytical Testing Results

In order to determine whether the spray drying led to decomposition of Compound 1, analytical testing was carried out on the solutions before spray drying and the spray dried powder. In each case, the content of Compound 1 in the sample was measured, as was the content of degradation products.

Analysis was carried out by HPLC using the analytical method set out above.

Analytical testing results for the spray dried compositions of lots 020 and 021 (Examples 6F and 6G) are presented in Table 3, those for lots 022 and 023 (Examples 6H and 6I) in Table 4 and those for Lots 031 to 033 (Examples 6L, 6M, 6N and 6O) in Table 5.

In the tables, the "solution" is the solution before spray drying and the content of Compound 1 was measured by HPLC and is presented in the table as a percentage of the calculated content of Compound 1.

The content of Compound 1 in the spray dried powder was also measured. In order to do this, the powder was taken up in a 30:70 mixture of phosphate buffer (pH 8.0) and acetonitrile and the solution analysed by HPLC to determine the amount of Compound 1 present.

In the tables, the "related substances" are degradation products of Compound 1 and "largest" refers to the largest HPLC peak.

TABLE 3

Analytical Results for Lots 020 and 021

| Parameter | Lot 020-2 (HPMC) | | Lot 021-2 (PVP) | |
|---|---|---|---|---|
| | Solution | Powder | Solution | Powder |
| Drug Load (%) | 40 | 40 | 40 | 40 |
| Appearance | Clear solution with a few fine particles in the bottom | Pale-Yellow powder/flakes | Clear solution with a few fine particles in the bottom | Pale-Yellow powder/flakes |
| Assay (%) | 102.8 | 90.8 | 97.2 | 92.5 |
| Related Substances (%) | Total: 1.25 Largest: 0.35 (RRT 0.81) | Total: 1.41 Largest: 0.22 (RRT 0.81) | Total: 0.64 Largest: 0.12 (RRT 2.12) | Total: 0.68 Largest: 0.11 (RRT 2.12) |
| Water Content (%) | NA | 1.0 | NA | 2.1 |

TABLE 4

Analytical Results for Lots 022 and 023

| Parameter | Lot 022 (HPMC) | | Lot 023 (PVP) | |
|---|---|---|---|---|
| | Solution | Powder | Solution | Powder |
| Drug Load (%) | 30 | 30 | 30 | 30 |
| Appearance | Clear solution with a few fine particles in the bottom | Pale-Yellow powder/flakes | Clear solution with a few fine particles in the bottom | Pale-Yellow powder/flakes |
| Assay (%) | 99.2 | 84.4 | 109.4 | 91.8 |
| Related Substances (%) | Total: 1.78 Largest: 0.41 (RRT 0.81) | Total: 3.07 Largest: 0.68 (RRT 0.81) | Total: 0.63 Largest: 0.17 (RRT 0.81) | Total: 0.28 Largest: 0.10 (RRT 0.80) |

TABLE 5

Analytical Results for Lots 031 to 033

| Parameter | Lot 031 (PVP) | Lot 032 (HPMC) | Lot 033 (PVP) |
|---|---|---|---|
| Drug Load (%) | 20 | 20 | 20 |
| Appearance | Pale-Yellow powder/flakes | Pale-Yellow powder/flakes | Pale-Yellow powder/flakes |
| Assay (%) | 97.8 | 91.5 | 98.0 |
| Related Substances (%) | Total: 0.71 Largest: 0.15 (RRT 0.81) | Total: 3.12 Largest: 1.07 (RRT 0.81) | Total: 0.52 Largest: 0.15 (RRT 0.81) |
| Water Content (%) | 2.1 | Not tested | 2.1 |
| Residual Solvent (µg/g) | MeOH: 75 DCM: N/De DMSO: 65320 Acetone: 10 | MeOH: 3 DCM: N/De DMSO: 46881 Acetone: 9 | Not tested |

From Tables 3 to 5, it appears that HPMC SDI at 40 (Table 3), 30 (Table 4), or 20% API (Table 5) generally has a lower assay and higher total related substances when compared to PVP SDI at comparable drug load.

EXAMPLE 9

Stability Under Controlled Storage Conditions

Samples from lots 022 (Example 6H; HPMC SDI 30% Compound 1) and 023 (Example 6I; PVP SDI 30% Compound 1) were incubated under different stability conditions: long term (25° C./60% RH), accelerated (40° C./75% RH) and at 50° C./Ambient stability conditions for verification of amorphous state stability. The bulk powder was packaged in open and closed 50 cc HDPE bottles. The short-term stability study was conducted according to the stability protocol described in Table 6. The samples were evaluated by XRPD for amorphous state and by HPLC for assay/degradation products at time zero and at subsequent time points.

TABLE 6

Stability Protocol, Spray Dried Compound 1, Lots 022 and 023

| Lots | Packaging material | T (° C.) 25 | 40 | 50 | Humidity (%) 60 | 75 | Amb (≤10%) |
|---|---|---|---|---|---|---|---|
| Lot 022 (Example 6H; HPMC SDI 30% Compound 1) | Open cap 50 cc HDPE bottle | ✓ | ✓ | | ✓ | ✓ | |
| Lot 023 (Example 6I; PVP SDI 30% Compound 1) | | ✓ | ✓ | | ✓ | ✓ | |
| Lot 022 (Example 6H; HPMC SDI 30% Compound 1) | Closed cap 50 cc HDPE bottle | ✓ | ✓ | ✓ | ✓ | ✓ | ✓ |
| Lot 023 (Example 6I; PVP SDI 30% Compound 1) | | ✓ | ✓ | ✓ | ✓ | ✓ | ✓ |

Figure 7:
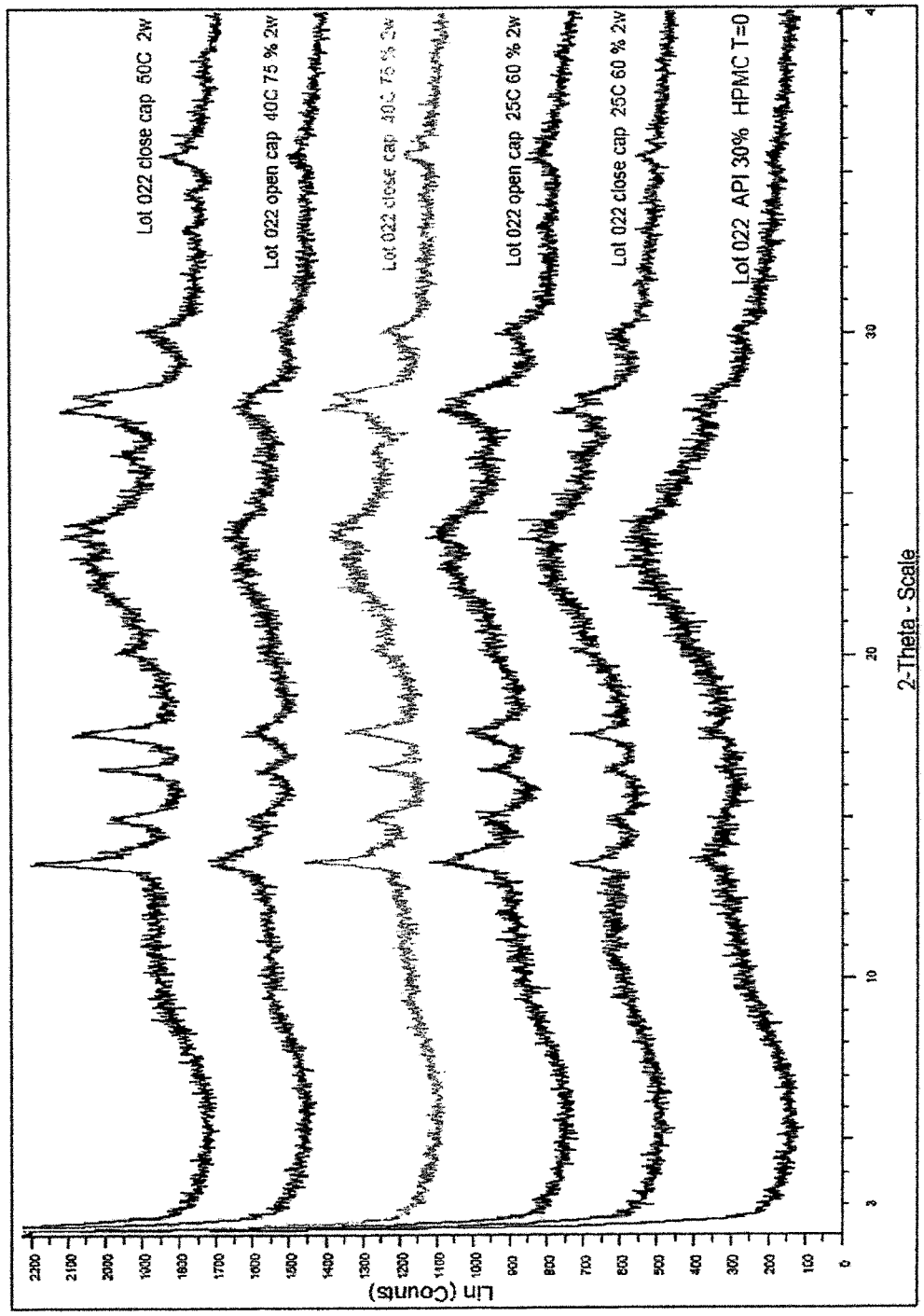
FIG. 7 shows XRPD patterns of initial and stability samples of 30% drug load HPMC spray-dry intermediates.
Figure 8:
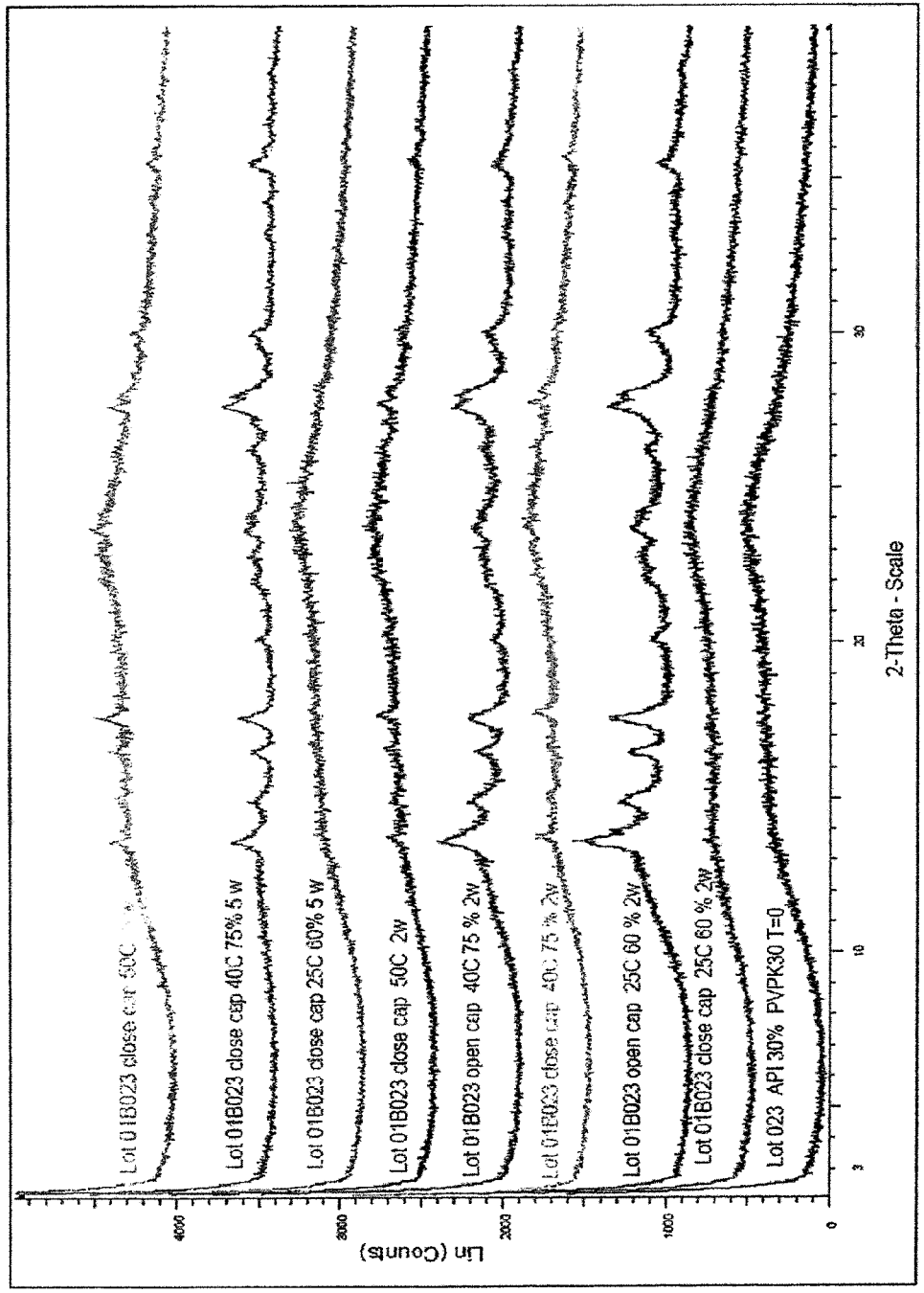
FIG. 8 shows XRPD patterns of initial and stability samples of 30% drug load PVP spray-dry intermediates.

XRPD patterns of initial and stability samples of 30% drug load HPMC and PVP SDI are shown in FIGS. 7 and 8 respectively. The 2-weeks stability samples showed characteristic peaks of crystalline OC000459 under all conditions tested for the HPMC SDI which indicated partial recrystallization of the amorphous form during storage (FIG. 7). However, XRPD patterns of initial and 2-weeks closed cap stability samples of PVP SDI showed no sign of recrystallization in stability samples (FIG. 8). For both, HPMC and PVP SDI samples exposed to heat and/or moisture (open cap condition), conversion into crystalline form was observed. XRPD data for PVP SDI (lot 023) 5 weeks-stability samples are shown in FIG. 8. There was no change in XRPD pattern for the sample stored at 25° C./60% RH (closed cap) during 5 weeks. This confirms the stability of the amorphous form under these conditions. XRPD data for 50° C. sample showed similar diffractogram compared to the 2-weeks stability sample with minor increase in peak intensity. This increase was lower than that observed for 40° C./75% RH-closed cap sample suggesting that moisture content contributes to recrystallization of amorphous form.

Assay/Related substances of initial and stability samples of 30% drug load HPMC and PVP SDI (lots 022 and 023) are tabulated in Tables 7 and 8, respectively.

TABLE 7

Compound 1 HPMC SDI, Lot 022, Stability Samples analytical Testing Results

| | | Sample Lot 022 (HPMC) Stability Condition | | | | |
|---|---|---|---|---|---|---|
| | | 25° C./60% R.H. Closed Cap | 25° C./60% R.H. Open Cap | 40° C./75% R.H. Closed Cap | 40° C./75% R.H. Open Cap | 50° C./Amb R.H. Closed Cap |
| Drug Load (%) | | 30 | 30 | 30 | 30 | 30 |
| Appearance | T = 0 | | Pale-Yellow powder/flakes | | | |
| | T = 2 wks | Pale-Yellow powder/flakes | Pale-Yellow powder/flakes | Pale-Yellow powder/flakes | Pale-Yellow powder flakes | Pale-Yellow powder flakes |
| Assay (%) | T = 0 | | | 84.4 | | |
| | T = 2 wks | 82.0 | 85.1 | 78.8 | 84.7 | 79.8 |
| Related Substances (%) | T = 0 | | Total Impurities: 3.07 Largest. 0.68 (RRT 0.81) | | | |
| | T = 2 wks | Total: 4.19 Largest: 1.22 (RRT 1.78) | Total: 4.35 Largest: 1.17 (RRT 1.78) | Total: 5.92 Largest: 1.98 (RRT 1.78) | Total: 4.27 Largest: 1.12 (RRT 1.78) | Total: 5.78 Largest: 1.76 (RRT 1.78) |

As observed previously, HPMC SDI appears to have a lower assay and higher total related substances values when compared to PVP SDI. Assay of 2-week HPMC samples stored at 25° C./60% R.H. and 40° C./75% R.H. (open cap) were similar to initial sample (T=0). For closed-cap samples the assay values were lower. Related substances increased for all samples. Assays of PVP SDI samples were quite stable after 2 weeks storage in closed container. Related substances increased for all samples.

The 4-week timepoint was not analyzed for the HMPC SDI (lot 022). Assay values of 4-weeks stability testing of PVP SDI stored at 25° C./60% R.H. and 50° C./<10% RH in closed HPDE bottle were comparable to T=0 but lower for the sample stored at 40° C./75% R.H. The related substances did not increase at any condition when compared with the values at the 2 week time point.

TABLE 8

Compound 1 PVP SDI, Lot 023, Stability Samples analytical Testing Results

| | | Sample Lot 023 (PVP) Stability Condition | | | | |
|---|---|---|---|---|---|---|
| | | 25° C./60% R.H. Closed Cap | 25° C./60% R.H. Open Cap | 40° C./75% R.H. Closed Cap | 40° C./75% R.H. Open Cap | 50° C./Amb R.H. Closed Cap |
| Drug Load (%) | | 30 | 30 | 30 | 30 | 30 |
| Appearance | T = 0 | | Pale-Yellow powder/flakes | | | |
| | T = 2 wks | Pale-Yellow powder/flakes | Pale-Yellow powder/flakes | Pale-Yellow powder/flakes | Pale-Yellow powder/flakes | Pale-Yellow powder/flakes |
| | T = 4 wks | Pale-Yellow powder/flakes | Not Tested | Pale-Yellow powder/flakes | Not Tested | Pale-Yellow powder/flakes |

TABLE 8-continued

Compound 1 PVP SDI, Lot 023, Stability Samples analytical Testing Results

|  |  | Sample Lot 023 (PVP) Stability Condition | | | | |
|---|---|---|---|---|---|---|
|  |  | 25° C./60% R.H. Closed Cap | 25° C./60% R.H. Open Cap | 40° C./75% R.H. Closed Cap | 40° C./75% R.H. Open Cap | 50° C./Amb R.H. Closed Cap |
| Assay | T = 0 |  |  | 91.8 |  |  |
| (%) | T = 2 wks | 90.7 | 83.4 | 89.3 | 83.0 | 91.5 |
|  | T = 4 wks | 90.5 | Not Tested | 84.1 | Not Tested | 94.3 |
| Related | T = 0 | Total Impurities: 0.28% Largest: 0.10% (RRT 0.81) | | | | |
| Substances | T = 2 wks | Total: 1.07 | Total: 1.00 | Total: 1.30 | Total: 0.96 | Total: 1.51 |
| (%) |  | Largest: 0.31 (RRT 1.78) | Largest: 0.29 (RRT 1.78) | Largest: 0.44 (RRT 1.78) | Largest: 0.25 (RRT 1.78) | Largest: 0.52 (RRT 1.78) |
|  | T = 4 wks | Total: 0.81 Largest: 0.21 (RRT 0.81) | Not Tested | Total: 0.97 Largest: 0.24 (RRT 0.81) | Not Tested | Total: 0.90 Largest: 0.28 (RRT 0.81) |

Also, samples from lot 031 (Example 6M; PVP SDI 20% Compound 1) were incubated under long term (25° C./60% RH) and accelerated (40° C./75% RH) ICH stability conditions. Samples from lots 033 (Example 6O; PVP SDI 20% Compound 1) were incubated at 4° C. and 50° C. The bulk powder was packaged in double PE bags with a desiccant in sealed aluminium bag into the HDPE bottle. The short-term stability study was conducted according to the stability protocol described in Table 9.

TABLE 9

Stability Protocol, Spray Dried Compound 1, Lots 031 and 033

| Lots | Packaging material | T (° C.) | | | | Humidity (%) | | | Amb (≤10%) |
|---|---|---|---|---|---|---|---|---|---|
|  |  | 4 | 25 | 40 | 50 | Amb | 60 | 75 |  |
| Lot 031 (Example 6M; PVP SDI 20% Compound 1) | Double PE bags with a desiccant in a sealed aluminium bag into HDPE bottle |  | ✓ |  |  |  | ✓ |  |  |
| Lot 031 (Example 6M; PVP SDI 20% Compound 1) |  |  |  | ✓ |  |  |  | ✓ |  |
| Lot 033 (Example 6O; PVP SDI 20% Compound 1) |  | ✓ |  |  |  | ✓ |  |  |  |
| Lot 033 (Example 6O; PVP SDI 20% Compound 1) |  |  |  |  | ✓ |  |  |  | ✓ |

As shown in FIG. 9, stability of the amorphous form of Compound 1 (20% with PVP) after 2, 4 and 12 weeks at 25° C./60% RH, 40° C./75% RH and at 50° C. was verified by XRPD and no changes were observed in their amorphous character. The chemical stability was also verified. The assay for both lot 031 and lot 033 and related substances for lot 031 remained similar to T=0 for up to 12 weeks. The amount of related substances increasing slightly for lot 033 but decreasing for lot 031. Water content in the stability samples was increased by approximately 2-3%.

After 6 months, only lot 031 was tested. When stored for 6 months at 25° C./60% RH and 40° C./75% RH lot 31 remained stable as judged by amorphous content, assay and impurity content, although there was a very small increase in total impurities at the accelerated condition (0.71% to 0.97% area). Assay values were not significantly changed from initial and there was no change in the X-ray amorphous content (FIG. 10). The results show that the amorphous Compound 1 stabilized with PVP is able to withstand accelerated storage conditions for at least 6 months when protected against moisture ingress.

TABLE 10

Compound 1/PVP Lots 031 and 033 Stability Testing Results

| | | Sample | | |
|---|---|---|---|---|
| | | L047-01B031 | | L047-01B033 |
| | | Dose strength | | |
| | | 20% | | 20% |
| Stability Condition | | 25° C./60% R.H. | 40° C./75% R.H. | 50° C./Amb R.H. |
| Appearance Visual Organoleptic | T = 0 | Pale-Yellow powder/flakes | | Pale-Yellow powder/flakes |
| | T = 0.5 mth | Not Tested | Pale-Yellow flakes and clumps | Pale-Yellow powder/flakes |
| | T = 1 mth | Not Tested | Yellow clumps | Pale-Yellow powder/flakes |
| | T = 3 mth | Pale-Yellow flakes and clumps | Yellow clumps | Pale-Yellow powder/flakes |
| | T = 6 mth | Pale-Yellow flakes and clumps | Yellow clumps | Not tested |
| Assay (%) | T = 0 | 97.8 | | 98.0 |
| | T = 0.5 mth | Not Tested | 97.3 | 98.0 |
| | T = 1 mth | Not Tested | 97.6 | 98.3 |
| | T = 3 mth | 96.9 | 97.3 | 98.4 |
| | T = 6 mth | 97.3 | 97.0 | Not tested |
| Water content (% w/w) Karl Fisher Titration | T = 0 | 2.1 | | 2.1 |
| | T = 0.5 mth | Not Tested | 3.6 | 3.9 |
| | T = 1 mth | Not Tested | 4.2 | 4.4 |
| | T = 3 mth | 4.1 | 5.5 | 5.1 |
| | T = 6 mth | 4.8 | 5.9 | Not tested |
| Related Substances (%) | T = 0 | Total: 0.71% Single largest impurity: 0.15% @ RRT 0.80 | | Total: 0.52% Single largest impurity: 0.15% @ RRT 0.80 |
| | T = 0.5 mth | Not Tested | Total: 0.65% Single largest impurity 0.14% @ RRT 0.80 | Total: 0.65% Single largest impurity 0.17% @ RRT 0.80 |
| | T = 1 mth | Not Tested | Total: 0.72% Single largest impurity 0.14% @ RRT 0.80 | Total: 0.71% Single largest impurity 0.18% @ RRT 0.80 |
| | T = 3 mth | Total: 0.47% Single largest impurity 0.12% @ RRT 0.80 | Total: 0.57% Single largest impurity 0.16% @ RRT 0.80 | Total: 0.63% Single largest impurity 0.21% @ RRT 0.80 |
| | T = 6 mth | Total: 0.79% Single largest impurity 0.14% @ RRT 0.80 | Total: 0.97% Single largest impurity 0.20% @ RRT 0.80 | Not tested |

EXAMPLE 10

Solubility in Aqueous Solutions

Crystalline and amorphous Compound 1/polymer formulation solubility was determined in different aqueous media (Tables 8A and 8B).

As shown in Table 11A, the highest concentrations were observed for non-spray-dried Compound 1 sodium salt. As mentioned earlier, the high solubility of the Compound 1 sodium salt most probably resulted from the conversion of the Compound 1 to its ionized form. In relation to crystalline Compound 1 (as-received sample), formulations containing amorphous form (Tables 11A and 11B) were more soluble than crystalline form under all studied conditions. Highest concentrations were observed in sodium buffer pH 8.0 with 2% SDS.

TABLE 11A

Compound 1 Solubility (mg/mL) Testing Results

| | ID/API % | | | | |
|---|---|---|---|---|---|
| Media | Compound 1* 100% | Compound 1 Sodium salt 100% | Lot 002 SD-sodium salt 100% | Lot 015-1 SD-HPMC 10% | Lot 020-1 SD-HPMC 40% |
| Water | 0.0006 | 15.37 | 16.87 | 0.0142 | 0.0066 |
| pH 1.0 | 0.0021 | 0.0036 | 0.0091 | 0.1712 | Not tested |
| pH 4.5 | 0.0019 | 2.605 | 0.0050 | 0.0066 | Not tested |
| pH 6.8 Na | 0.0000 | 2.487 | 0.0006 | 0.0947 | Not tested |
| pH 6.8 K | 0.0003 | 8.554 | 0.0002 | 0.0658 | Not tested |
| pH 8.0 Na | 0.0003 | 1.744 | 1.782 | 0.1838 | 0.2140 |
| pH 8.0 K | 0.0008 | 5.571 | 2.740 | 0.2508 | Not tested |
| Water + 1% SDS | Not tested | >30 | >17 | 0.0518 | 0.0529 |
| Water + 1% Tween 20 | Not tested | >26 | >22 | 0.0120 | Not tested |
| Water + 1% Tween 80 | Not tested | >21 | >14 | 0.0097 | Not tested |
| pH 6.8 + 1% HTAB | Not tested | 4.114 | 3.597 | >0.4 | Not tested |
| pH 6.8 + 1% Tween 20 | Not tested | 0.1275 | 0.1623 | 0.1492 | Not tested |
| pH 6.8 + 1% Tween 80 | Not tested | 3.216 | 0.2260 | 0.0877 | Not tested |
| pH 8.0 Na + 2% SDS | Not tested | Not tested | Not tested | Not tested | 0.6987 |

*Standard Corrected Purity: 98.6%

TABLE 11B

Compound 1 Solubility (mg/mL) Testing Results

| | ID/API % | | | | |
|---|---|---|---|---|---|
| Media | Lot 021-1 SD-PVPK30 40% | Lot 020-2 SD-HPMC 40% | Lot 21-2 SD-PVPK30 40% | Lot 022 SD-HPMC 30% | Lot 023 SD-PVPK30 30% |
| Water | 0.0036 | 0.0074 | 0.0008 | 0.0045 | 0.0009 |
| pH 6.8 Na | 0.0347 | 0.0421 | 0.0796 | 0.0404 | 0.0172 |
| pH 8.0 Na | Not tested | 0.0138 | 0.0104 | 0.0322 | 0.0230 |
| Water + 1% SDS | 0.2227 | 0.1107 | 0.1625 | 0.1348 | 0.2298 |
| pH 8.0 Na + 2% SDS | 0.8359 | 0.5195 | 0.4859 | 0.5751 | 0.9587 |

The data in Table 12 show that water solubility increases dramatically for Compound 1 sodium salt in relation to Compound 1 as-received. Overall, Compound 1 amorphous forms also showed an increase in water solubility compared to the crystalline form. Given the limited number of experiments performed, the PVP SDI (10:90 drug to polymer ratio) lot 019 showed the greater increase in water solubility. At drug load of 20% or more, HPMC appeared to improve the solubility better when compared to PVP. Also, it appeared that a higher proportion of polymer generally improved the solubility of Compound 1.

The formulation containing Gelucire 44/14 (50%)/PEG400 (30%) (lot 027) did not improve solubility of Compound 1 in water (Table 12) which is consistent with the fact that the API remained crystalline.

TABLE 12

Water Solubility Increases for Compound 1

| ID | Note/Excipient | API (%) | Solubility in water (mg/mL) | Increase in water solubility (%) |
|---|---|---|---|---|
| Compound 1 | N/A | 100 | 0.0006 | NA |
| Compound 1 sodium salt | Sodium salt | 100 | 15.37 | 2561667 |
| Lot 002 (Comp. Example 3B) | Spray-Dried Na salt | 100 | 16.87 | 2811667 |
| Lot 019 (Example 6E) | PVP | 10 | 0.0268 | 4467 |
| Lot 015-1 (Example 6B) | HPMC | 10 | 0.0142 | 2367 |
| Lot 032 (Example 6N) | HPMC | 20 | 0.0184 | 3067 |
| Lot 031 (Example 6M) | PVP | 20 | 0.0100 | 1667 |
| Lot 022 (Example 6H) | HPMC | 30 | 0.0045 | 750 |
| Lot 023 (Example 6I) | PVP | 30 | 0.0009 | 150 |
| Lot 020-1 (Example 6F-1) | HPMC | 40 | 0.0066 | 1100 |
| Lot 021-1 (Example 6G-1) | PVP | 40 | 0.0036 | 600 |
| Lot 020-2 (Example 6F-2) | HPMC | 40 | 0.0074 | 1233 |
| Lot 021-2 (Example 6G-2) | PVP | 40 | 0.0008 | 133 |
| Lot 027 (Comp. Example 5K) | Gelucire | 20 | 0.0006 | 100 |

EXAMPLE 11

Solubility in Simulated Gastric and Intestinal Fluids

The solubilization profile was obtained of various compositions in USP Simulated Gastric Fluid (SGF) and USP Simulated Intestinal Fluid (SIF) with pH 1.2 and 6.8, respectively. Although neither are exact reproductions of physiological media, it was decided to evaluate the solubility with the media maintained at 37° C., with gentle shaking, and sampling at various time points up to 60 minutes. The concentration of the solution was based on the hypothesis that the test should simulate a dissolution test for a 100 mg dose strength tablet or capsule in 900 ml of dissolution media.

The solubility was tested for the crystalline compound 1 with a purity of 98.9%, and for the amorphous compositions of Examples 6M and 6O (Lots 031 and 033).

The following procedure was followed:
A shaking water bath was filled and water temperature left to equilibrate to 37° C. for 24 hours.

USP simulated gastric fluid was prepared as described in the UPS 31, Solutions: Test solutions.

USP simulated intestinal fluid was prepared as described in the UPS 31, Solutions: Test solutions.

The equivalent of 12.5 mg of Compound 1 was weighed and transferred into a 125 mL Erlenmeyer flask, with 100 mL of medium. This is equivalent to 1×100 mg dose strength tablet in 900 mL of dissolution medium.

The flasks were mounted to the submerged shaker.

The shaker was set to a linear motion equivalent to 1 directional movement per second.

Using a probe with a 45 μm filter, samples were taken after 5, 10, 15, 30 and 60 min and injected in the HPLC The amount of dissolved material was determined with respect to a standard and is reported as the percentage of material dissolved with respect to the standard as well as in absolute mg/ml. The theoretical concentrations of the standard and the samples are presented in Table 13.

TABLE 13

Theoretical Standard and Sample Concentrations

| Sample Description | Diluent | Theoretical Concentration (mg/ml) |
|---|---|---|
| HPLC standard A | Mobile Phase | 0.12093 |
| Crystalline Compound 1 | SGF | 0.12009 |
| Lot 031 (Example 6M) | SGF | 0.11762 |
| Lot 033 (Example 6O) | SGF | 0.12866 |
| Crystalline Compound 1 | SIF | 0.12207 |
| Lot 031 (Example 6M) | SIF | 0.11684 |
| Lot 033 (Example 6O) | SIF | 0.12378 |

The solubility profiles of the samples are presented in FIGS. 10 and 11 representing SGF and SIF respectively. As expected the API shows very poor solubility under these pH conditions. This has been demonstrated previously. However, the amorphous spray dried material shows significantly better solubility, with both lots achieving close to 90% dissolution in SGF. It is odd, however, that Lot 031 (Example 6M) showed only 50% dissolution on SIF. This is unexpected for several reasons: 1) both Lots 031 and 033 are very similar in nature, using the same polymer and solvent during the manufacturing process, and 2) solubility would have been expected to be higher at the higher pH level.

Visually, the solutions were not clear, and still contained material in suspension. In the case of the pure API, it is assumed that this is the API itself in suspension. In the case of the SDI, the material in suspension is mostly polymer. This makes it extremely difficult to visually determine if the entire active has been solubilized or not. However, the filtrate injected into the HPLC was limpid, although it may be possible that a small amount of the SDI material may have passed the 45 micron filter. No further dilution of the sample was performed prior to injection.

As a result, it is quite possible that the low solubility results for Lot 031 in SIF could be a manipulation error. It is also interesting to note that complete solubility seems to be achieved very quickly. The profiles show a small drop in solubility after 60 minutes, which may suggest some precipitation.

EXAMPLE 12

Further Amorphous Compositions

In an attempt to investigate the use of other polymers and to adjust the reaction protocol to minimise the amount of solvent used, further experiments were conducted and Lots C005 to C010 were prepared by spray-drying from solutions produced by the method set out below.

Solutions of Compound 1 were prepared using appropriately sized three neck flasks equipped with a reflux column, addition funnel and thermometer. DMSO was added in to the flask and kept under continuous magnetic stirring. Polymer and Compound 1 were subsequently added into the flask. Using a dry sand bath, the solution was slowly heated to about 100° C. and kept at this temperature until a clear yellow solution was obtained. While still heating the solution, acetone was slowly added into the flask. The solution under reflux was cooled down between 55-60° C. and maintained at this temperature during the spray drying process. The solution was spray dried using a Mini Spray Dryer model B-290 (Buchi) equipped with 1.5 mm nozzle and the operating parameters presented below. After the spray drying the solution, the heater was stopped but the air flow was maintained until a final outlet temperature of 30-40° C. (about 15 min) was reached. The collected Compound 1 spray dried intermediates were immediately stored in hermetically closed amber glass bottle. Note that for lots C009 and C010, the filtration unit of the spray dryer was modified to avoid decreased of the air flow rate (inducing a lower outlet temperature) associated with the accumulation of powder on the filter. The cyclone and product collection vessel assembly was also isolated with glass wool.

Lot C005
Prepared from 10 g Compound 1 and 40 g PVP K30, spray dried from a mixture of 325 ml acetone and 175 ml DMSO.
Compound 1:PVP K30=20:80.
Spray dryer operational parameters:

| Inlet temperature | 220 ± 2° C. |
| Outlet Temperature | 122 ± 2° C. |
| Atomization flow (NL/h) | 473 (approx.) |
| Air flow (m$^3$/h) | 38 (approx.) |
| Feed rate (ml/min) | 12.5 |

Lot C006
Prepared from 5 g Compound 1 and 20 g PVP K30, spray dried from a mixture of 162.5 ml acetone and 87.5 ml DMSO.
Compound 1:PVP K30=20:80.
Spray dryer operational parameters:

| Inlet temperature | 220 ± 2° C. |
| Outlet Temperature | 122 ± 2° C. |
| Atomization flow (NL/h) | 414 (approx.) |
| Air flow (m$^3$/h) | 38 (approx.) |
| Feed rate (ml/min) | 10 |

Lot C007
Prepared from 5 g Compound 1 and 20 g Kollidon® VA64 spray dried from a mixture of 162.5 ml acetone and 87.5 ml DMSO.
Compound 1:PVP-VA=20:80
Spray dryer operational parameters:

| Inlet temperature | 220 ± 1° C. |
| Outlet Temperature | 121 ± 1° C. |
| Atomization flow (NL/h) | 414 (approx.) |
| Air flow (m$^3$/h) | 38 (approx.) |
| Feed rate (ml/min) | 9.6 |

Lot C008
Prepared from 10 g Compound 1 and 15 g PVP K30, spray dried from a mixture of 325 ml acetone and 175 ml DMSO.
Compound 1: PVP K30=40:60.
Spray dryer operational parameters:

| Inlet temperature | 220 ± 1° C. |
| Outlet Temperature | 124 ± 3° C. |
| Atomization flow (NL/h) | 414 (approx.) |
| Air flow (m$^3$/h) | 38 (approx.) |
| Feed rate (ml/min) | 8.9 |

Lot C009
Prepared from 22 g Compound 1 and 33 g PVP K30, spray dried from a mixture of 715 ml acetone and 385 ml DMSO.
Compound 1: PVP K30=40:60.
Spray dryer operational parameters:

| Inlet temperature | 221 ± 1° C. |
| Outlet Temperature | 128 ± 2° C. |
| Atomization flow (NL/h) | 473 (approx.) |
| Air flow (m$^3$/h) | 38 (approx.) |
| Feed rate (ml/min) | 9.7 |

Lot C010
Prepared from 20 g Compound 1 and 30 g Kollidon® VA64 spray dried from a mixture of 650 ml acetone and 350 ml DMSO.
Compound 1:PVP-VA=40:60.
Spray dryer operational parameters:

| Inlet temperature | 219 ± 2° C. |
| Outlet Temperature | 130 ± 4° C. |
| Atomization flow (NL/h) | 414 (approx.) |
| Air flow (m$^3$/h) | 38 (approx.) |
| Feed rate (ml/min) | 9.3 |

XRPD studies showed that in all of these compositions, Compound 1 was present in an amorphous form.

EXAMPLE 13

Stability Study

To evaluate the stability of the compositions of Example 12, three spray dried formulations were selected:
Lot C007 (OC000459/Kollidon VA64 20/80 w/w);
Lot C008 (OC000459/PVP K30 40/60 w/w);
Lot C010 (OC000459/Kollidon VA64 40/60 w/w).

All lots were vacuum dried at 50° C., −20 mmHg for 72 h prior to the initiation of the stability study. For lot C007, samples were only incubated at 5° C. and 40° C./75% RH due to the small quantity of material available. For lots C008 and C010 samples were incubated at 5° C./ambient, 25° C./60%, 40° C./75% and 50° C./ambient RH. All samples were stored in double polyethylene (PE) bags with a desiccant sachet between the two bags, sealed inside an aluminium bag put into 250 cc HDPE bottles. The bottles were capped with polypropylene caps followed by induction sealing and were placed into controlled environment chambers.

FIG. 13 presents XRPD of the three lots at T=0. At T=1 month, only the XRPD of lots C008 and C010 were carried out and their results are displayed in FIGS. 14 and 15, respectively. After 1 month, no significant changes of diffractograms were observed compared to T=0 at both accelerated and long-term stability conditions.

However, XRPD data revealed that after 3 months at 40° C./75% R.H. lot C010 showed definitive signs of re-crystallization when compared to lot C008 (FIG. 16). It appears that, under these conditions, Kollidon VA64 (lot C010) is less suitable as a stabilizer when compared to PVP K30 (lot C008) for amorphous Compound 1. Samples at other storage conditions did not appear to re-crystallize and remained amorphous.

Table 14 displays the analytical data of stability results for all lots at T=0 as well as data for lots C008 and C010 at 1 and 3 months, and data for lot C008 at 6 months under various storage conditions. Assay values remained constant for both lots C008 and C010 at all conditions through the 3-month time point. At 6 months, the assay results (not corrected for water content or residual solvent, Table 14) were in the range 90.0%-96.3%. At T=1-month, an increase of 2-2.5% in water content was observed for lots C008 and C010 compared to results at T=0. It was hypothesized that these observations may have been an analytical artefact due to the sample not having been analyzed promptly. However, following prompt analysis the 3-month time point samples also showed an increase when compared to T=0 (0.5-3.5%). This phenomenon was also observed in the stability study described in Example 9 with lots 031 and 033, which revealed that despite similar precautions to prevent moisture-ingress the SDI is a very hygroscopic material. The hygroscopic nature of the SDI was also noticeable at T=6-months, where an increase of 7.7% in water content was observed for lot C008 at 40° C./75% RH compared to results at T=0.

TABLE 14

Stability Results of OC000459 SDI Lots C007, C008 and C010

| Sample | | Lot C007 | | Lot C008 | | | Lot C010 | | |
|---|---|---|---|---|---|---|---|---|---|
| Drug Load (% w/w) | | 20% | | 40% | | | 40% | | |
| Stability Condition | | 5° C./ Amb RH | 40° C./ 75% RH | 5° C./ Amb RH | 25° C./ 60% RH | 40° C./ 75% RH | 5° C./ Amb RH | 25° C./ 60% RH | 40° C./ 75% RH |
| Appearance visual | T = 0† | Pale yellow powder | | Pale yellow powder | | | Pale yellow powder | | |
| | T = 1 mth | NT | | Pale yellow powder | | | Pale yellow powder | | |
| | T = 3 mth | NT | | Pale yellow powder | | | Pale yellow powder | | |
| | T = 6 mth | NT | | Pale yellow powder | | | NT | | |
| Assay (% of nominal content) | T = 0† | 101.3% | | 100.6% * | | | 98.7% * | | |
| | T = 1 mth | NT | ND | 109.6% ** | 100.5% ** | | ND | 98.5% ** | 99.6% ** |
| | T = 3 mth | NT | ND | 102.3% *** | 101.0% *** | | ND | 99.1% *** | 98.7% *** |
| | T = 6 mth | NT | 96.3% **** | | 95.9% **** | 90.0% **** | | | NT |
| Water Content (% w/w) Karl-Fischer | T = 0† | 2.4% | | 2.9% | | | 1.2% | | |
| | T = 1 mth | NT | NT | 5.4% | 4.9% | | NT | 3.2% | 3.4% |
| | T = 3 mth | NT | NT | 3.4% | 6.2% | | NT | 2.1% | 4.7% |
| | T = 6 mth | NT | NT | | 4.8% | 10.6% | | | NT |
| Related Substances (% area) | T = 0† | Total 0.17% Largest impurity 0.13% @ RRT 0.82 | | Total 0.19% Largest impurity 0.12% @ RRT 0.83 | | | Total 0.39% Largest impurity 0.15% @ RRT 0.83 | | |
| | T = 1 mth | NT | Total 0.32% Largest impurity 0.13% @ RRT 0.83 | Total 0.14% Largest impurity 0.07% @ RRT 0.83 | Total 0.14% Largest impurity 0.07% @ RRT 0.83 | | Total 0.53% Largest impurity 0.17% @ RRT 0.83 | Total 0.45% Largest impurity 0.16% @ RRT 0.83 | Total 0.47% Largest impurity 0.17% @ RRT 0.83 |
| | T = 3 mth | NT | Total 0.0.87% Largest impurity 0.13% @ RRT 2.08 | Total 0.34% Largest impurity 0.07% @ RRT 1.74 | Total 0.37% Largest impurity 0.09% @ RRT 0.83 | | Total 0.90% Largest impurity 0.15% @ RRT 0.83 | Total 0.99% Largest impurity 0.17% @ RRT 0.83 | Total 1.04% Largest impurity 0.20% @ RRT 0.83 |
| | T = 6 mth | NT | Total 0.44% Largest impurity 0.12% @ RRT 0.83 | | Total 0.52% Largest impurity 0.14% @ RRT 0.83 | Total 0.60% Largest impurity 0.19% @ RRT 0.83 | | | NT |
| Residual Solvents (ppm) | T = 0 | Acetone: ND DMSO: 17723 | | Acetone: ND DMSO: 33088 | | | Acetone: ND DMSO: 28600 | | |
| | T = 1 mth | NT | | NT | | | NT | | |

TABLE 14-continued

Stability Results of OC000459 SDI Lots C007, C008 and C010

| Sample | | Lot C007 | Lot C008 | | | | Lot C010 | |
|---|---|---|---|---|---|---|---|---|
| T = 3 mth | | NT | DMSO: 22278 | DMSO: 28434 | DMSO: 10207 | DMSO: 26136 | DMSO: 23739 | DMSO: 7948 |
| T = 6 mth | | NT | | NT | | | | NT |

†T = 0 corresponds to the Lot C007, C008 C010 Vacuum Dried at 50° C., −20 mmHg for 72 h;
\* Corrected using the T = 0 results for residual solvent and water content
\*\* Corrected using the T = 0 results for residual solvent and T = 1 month results for water content
\*\*\* Corrected using the T = 3 month results for residual solvent and T = 3 month results for water content as per the following equation:

$$\frac{\% \text{ Assay} \times 100}{100 - \% \text{ Moisture} - \% \text{ Residual Solvent}} = \% \text{ Label Claim Compd 1 'dried basis'}$$

\*\*\*\* Assay could not be corrected for water content and residual solvent because the latter was not determined.

The single largest impurity detected at RRT 0.83 for all lots did not show any noteworthy changes under the tested stability conditions after 3 months (lot C010) or 6 months (lot C008). There was an apparent increase in Total Impurity content after 3 months when compared to T=0 for both lots C008 and 010 at all conditions tested. An increase was also observed for Lot C008 at T=6 months at all conditions, although the magnitude of the increase at 5° C. was smaller. However, for lot C008 there was no significant increase in any individual impurity at either 25° 060% RH or 40° C./75% RH. For lot C010 at 3 months there was evidence of an increase in two impurities at RRT 1.74 and 2.01 when compared to the previous time points. The level for these two impurities at 3 months was essentially the same across all three storage conditions. It is therefore concluded that degradation of the sample had not occurred since the level for the two impurities showed no evidence of increase with storage temperature. In addition, this increase in Total Impurity content did not appear to be linked to any decrease in Assay. For both lots the Total Impurity content remained below the putative specification value of 2%.

The Examples demonstrate that an amorphous form of Compound 1 could be obtained by spray drying with HPMC PVP, PVP-VA; or HPMCAS.

The amorphous forms obtained by spray drying with PVP and HPMC had greatly improved solubility in aqueous solvents compared with the crystalline form. Higher solubility was obtained for formulations with higher concentrations of polymer. The formulation containing 10% Compound 1 and 90% PVP (Example 6E) had higher solubility in aqueous solvents than the equivalent formulation containing HPMC (Example 6B) but for higher concentrations of Compound 1, formulations containing HPMC generally had slightly greater solubility in aqueous solvents than formulations containing PVP.

Thus, both the form with PVP and that with HPMC had increased solubility in aqueous media.

Finally, the amorphous dispersion of Compound 1 in PVP proved to have significantly greater solubility in simulated gastric fluid and intestinal fluid than might have been expected.

The amorphous forms have been demonstrated to be stable over periods of up to 6 months, depending on the storage conditions and, indeed, may prove to be stable over longer periods than this.

The greatest stability is achieved with compositions comprising Compound 1 and PVP, especially PVP K30.

The invention claimed is:

1. Amorphous (5-Fluoro-2-methyl-3-quinolin-2-ylmethyl-indol-1-yl)-acetic acid (Compound 1) or a pharmaceutically or veterinarily acceptable salt thereof.

2. A method for the treatment of a disease or condition selected from the group consisting of asthma, asthma exacerbations, chronic obstructive pulmonary disease, allergic rhinitis conjunctivitis, nasal polyps, atopic dermatitis, contact hypersensitivity, eosinophilic cough, eosinophilic bronchitis, eosinophilic gastroenteritis, eosinophilic oesophagitis, food allergies, inflammatory bowel disease, ulcerative colitis, Crohn's disease, mastocytosis, urticaria, hypereosinophilic syndrome, hyper IgE syndrome, infection, fibrotic diseases, Churg-Strauss syndrome, and multiple sclerosis, comprising administering to a patient in need of such treatment an effective amount of an amorphous form of Compound 1 or a pharmaceutically or veterinarily acceptable salt thereof.

3. A pharmaceutical or veterinary composition comprising amorphous Compound 1 or a pharmaceutically or veterinarily acceptable salt thereof and a pharmaceutically acceptable excipient or carrier.

4. The composition as claimed in claim 3, further comprising one or more additional active agents selected from:
Suplatast tosylate and similar compounds;
β2 adrenoreceptor agonists such as metaproterenol, isoproterenol, isoprenaline, albuterol, salbutamol, formoterol, salmeterol, indacaterol, terbutaline, orciprenaline, bitolterol mesylate and pirbuterol or methylxanthines such as theophylline, oxitriphylline and aminophylline, mast cell stabilisers such as sodium cromoglycate or muscarinic receptor antagonists such as tiotropium, aclidinium and ipratorium;
antihistamines, for example histamine $H_1$ receptor antagonists such as loratadine, cetirizine, desloratadine, levocetirizine, fexofenadine, astemizole, azelastine, olopatadine and chlorpheniramine or $H_4$ receptor antagonists;
$\alpha_1$ and $\alpha_2$ adrenoreceptor agonists such as propylhexedrine phenylephrine, phenylpropanolamine, pseudoephedrine, naphazoline hydrochloride, oxymetazoline hydrochloride, tetrahydrozoline hydrochloride, xylometazoline hydrochloride and ethylnorepinephrine hydrochloride;
modulators of chemokine receptor function, for example CCR1, CCR2, CCR2A, CCR2B, CCR3, CCR4, CCR5, CCR6, CCR7, CCR8, CCR9, CCR10 and CCR11 (for the C—C family) or CXCR1, CXCR2, CXCR3, CXCR4 and CXCR5 (for the C—X—C family) and $CX_3CR1$ for the C—$X_3$—C family;

Leukotriene antagonists such as montelukast, pranlukast and zafirlukast leukotriene biosynthesis inhibitors such as 5-lipoxygenase inhibitors or 5-lipoxygenase activating protein (FLAP) inhibitors such as zileuton, atreleuton, fenleuton, tepoxalin, 1-[4-[5-(4-fluorophenoxy)furan-2-yl]but-3-yn-2-yl]1-hydroxyurea, N-(5-substituted)-thiophene-2-alkylsolfonamides, 2,6-di-tert-butylphenol hydrazones, methoxytetrahydropyrans such as 6-[[3-fluoro-5-(4-methoxyoxan-4-yl)phenoxy]methyl]-1-methylquinolin-2-one, 1-[(3S)-6-[(2,6-difluorophenyl)methoxy]-2,3-dihydro-1-benzofuran-3-yl]-1-hydroxyurea, pyridinyl-substituted-2-cyanonaphthalene compounds such as [1S,5R]-3-cyano-1-(3-furyl-6-{6-[3-(3α-hydroxy-6,8-dioxabicyclo[3.2.1]octanyl)]pyridin-2-ylmethoxy}naphthalene, 2-cyanoquinoline compounds such as [1S,5R]-2-cyano-4-(3-furyl)-7-3-fluoro-5-[3-(3α-hydroxy-6,8-dioxabicyclo[3.2.1]-octanyl)]phenoxymethyl quinoline, indole and quinolone compounds such as quiflapon, 1-[(4-chlorophenyl)methyl]-3-[(1,1-dimethylethyl)thio]-α,α-dimethyl-5-(1-methylethyl)-1H-indole-2-propanoic acid and (2R)-2-cyclopentyl-2-[(4-quinolin-2-ylmethoxy)phenyl]acetic acid;

Phosphodiesterase inhibitors, including PDE4 inhibitors such as roflumilast;

anti-IgE antibody therapies such as omalizumad;

anti-infectives such as fusidic acid (particularly for the treatment of atopic dermatitis);

anti-fungals such as clotrimazole (particular for the treatment of atopic dermatitis);

immunosuppressants such as tacrolimus and particularly pimecrolimus in the case of inflammatory skin disease or alternatively rapamycin, cyclosporine, azathioprine or methotrexate;

Immunotherapy agents including allergen immunotherapy such as Grazax; corticosteroids such as prednisone, prednisolone, flunisolide, ciclesonide, triamcinolone acetonide, beclomethasone dipropionate, budesonide, fluticasone propionate mometasone furoate and fluticasone furoate;

drugs which promote Th1 cytokine response such as interferons, TNF or GM-CSF; and therapies that are in development for inflammatory indications including:

other antagonists of PGD$_2$ acting at other receptors such as DP antogonists;

drugs that modulate cytokine production such as inbhitors of TNFα converting enzyme (TACE) anti-TNF monoclonal antibodies, TNF receptor immunoglobulin molecules, inhibitors of other TNF isoforms, non-selective COX-1/COX-2 inhibitors such as piroxicam, diclofenac, propionic acids such as naproxen, flubiprofen, fenoprofen, ketoprofen and ibuprofen, fenamates such as mefanamic acid, indomethacin, sulindac and apazone, pyrazolones such as phenylbutazone, salicylates such as aspirin; COX-2 inhibitors such as meloxicam, celecoxib, rofecoxib, valdecoxib and etoricoxib, low dose methotrexate, lefunomide, ciclesonide, hydroxychloroquine, d-penicillamine, auranofin or parenteral or oral gold;

drugs that modulate the activity of Th2 cytokines including IL-4, IL-5, IL-9, IL-13 and their receptors, for example blocking monoclonal antibodies (e.g. mepolizumab) and soluble receptors;

PPAR-γ agonists such as rosiglitazone, piaglitazone; or with anti-RSV antibodies such as Synagis (palivizumab) and agents that may be used to treat rhinovirus infection in the future e.g. interferon-alpha, interferon-beta or other interferons.

5. The composition as claimed in claim 4, wherein the additional active agent is selected from the group consisting of montelukast, pranlukast, zafirlukast, loratadine, cetirizine, desloratadine, levocetirizine, fexofenadine, astemizole, azelastine, olopatadine, and chlorpheniramine.

6. A method for the treatment of a disease or condition selected from the group consisting of asthma, asthma exacerbations, chronic obstructive pulmonary disease, allergic rhinitis conjunctivitis, nasal polyps, atopic dermatitis, contact hypersensitivity, eosiniphilic cough, eosinophilic bronchitis, eosinophilic gastroenteritis, eosinophilic oesophagitis, food allergies, inflammatory bowel disease, ulcerative colitis, Crohn's disease, mastocytosis, urticaria, hypereosinophilic syndrome, hyper IgE syndrome, infection, fibrotic diseases, Churg-Strauss syndrome, and multiple sclerosis, comprising administering to patient in need of such treatment an amorphous Compound 1 or a pharmaceutically or veterinarily acceptable salt thereof and one or more of the agents listed in claim 4.

7. A kit for the treatment of a disease or condition mediated by the action of PGD$_2$ at the CRTH2 receptor comprising a first container comprising an amorphous Compound 1 or a pharmaceutically or veterinarily acceptable salt thereof and a second container comprising one or more of the active agents listed in claim 4.

* * * * *